United States Patent [19]

Kluge et al.

[11] Patent Number: 4,608,388
[45] Date of Patent: Aug. 26, 1986

[54] NOVEL [4,2,0]BICYCLOOCTANE DERIVATIVES WITH VALUABLE THERAPEUTIC PROPERTIES

[75] Inventors: Arthur F. Kluge, Los Altos; Anthony L. Willis, Newark; Counde O'Yang, Mountain View, all of Calif.

[73] Assignee: Syntex (U.S.A.) Inc., Palo Alto, Calif.

[21] Appl. No.: 716,872

[22] Filed: Mar. 27, 1985

[51] Int. Cl.$^4$ .............................................. C07C 69/74
[52] U.S. Cl. .................................. 514/510; 514/511; 514/557; 514/703; 514/729; 560/119
[58] Field of Search ................. 560/119; 514/510, 511, 514/557, 703, 729

[56] References Cited

U.S. PATENT DOCUMENTS 4,306,076  12/1981  Nelson ................................ 560/56

FOREIGN PATENT DOCUMENTS 2424908  2/1979  France ............................. 514/510
2014143  8/1979  United Kingdom ............. 514/510

OTHER PUBLICATIONS

Morton et al, "J. Organic Chem.", vol. 44 (1979) p. 2880.
Aristoff et al, "J. Organic Chem.", vol. 48 (1983) 5341.
Crossley, "Tetrahedron Letters" (1971) p. 3327.
Corey et al, "Tetrahedron Letters" (1973) p. 3091.
Kojima et al, "Tetrahedron Letters" (1978) p. 3743.
Shibasaki et al, "Tetrahedron Letters" (1979) p. 433.

*Primary Examiner*—Werren B. Lone
*Attorney, Agent, or Firm*—Ellen J. Wise; Tom M. Moran; Alan M. Krubiner

[57] ABSTRACT

Compounds useful in treating cardiovascular disorders such as thrombosis, hypertension, and atherosclerosis are compounds depicted in formulas (1), (2), and (3):

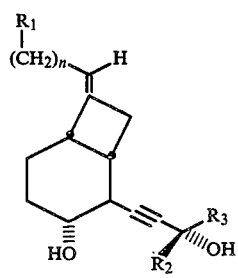

(1)

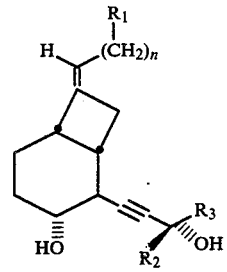

(2)

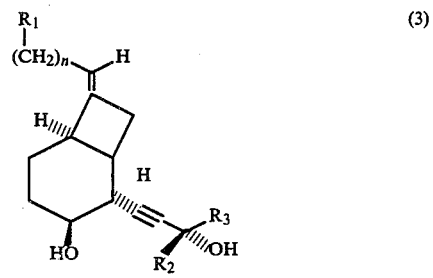

(3)

wherein:
n is 2 or 3;
$R_1$ is $CH_2OH$, CHO, $CO_2R$ or $CO_2H$;
$R_2$ is hydrogen or methyl; and
$R_3$ is linear or branched alkyl having 5-10 carbon atoms,

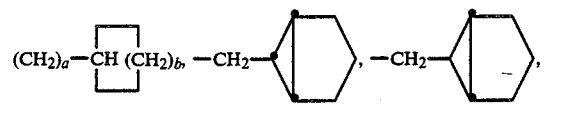

optionally substituted with lower alkyl, lower alkoxy, trifluoromethyl, or halogen,
in which
a is 0, 1 or 2;
b is 3-7;
m is 1 or 2; and
R is

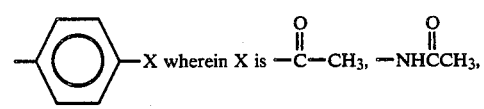

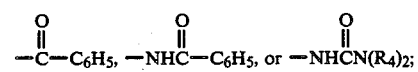

in which each $R_4$ is independently hydrogen or lower alkyl having 1-6 carbon atoms,
and the pharmaceutically acceptable, non-toxic salts and esters thereof.

55 Claims, No Drawings

NOVEL [4,2,0]BICYCLOOCTANE DERIVATIVES WITH VALUABLE THERAPEUTIC PROPERTIES

BACKGROUND OF THE INVENTION

1. Field of the Invention

This invention concerns novel derivatives of certain bicyclo[4.2.0]octanes and pharmaceutically acceptable salts and esters thereof, their use in treating cardiovascular disorders, pharmaceutical compositions containing these compounds, and methods of preparing such compounds.

2. Related Disclosures

Bicyclo[4.2.0]oct-2-en-7-one is readily prepared from 1,3-cyclohexadiene (*Tetrahedron*, 27:615, 1971). This has been used as an intermediate in a prostaglandin syntheses (*Tetrahedron Lett.*, 3091, 1973).

Several prostaglandin analogues are known which contain bicyclic all-carbon skeletons. Carbacyclin contains a bicyclo[3.3.0]octane skeleton, and is described in several publications (*J. Chem. Soc., Chem. Commun.*, 1067, 1978, *Tetrahedron Lett.*, 3743, 1978; *Tetrahedron Lett.*, 433, 1979; *Tetrahedron Lett.*, 2807, 1979; *J. Org. Chem.* 44:2880, 1979) and patents (Belgium Pat. No. 874, 135; British Pat. No. 2,014,143; French Pat. No. 2,424,908; Ger. Offen. No. 2,904,655; Japanese Pat. No. K 79,117,450; Netherland Patent Application Nos. 7,901,076 and 8,003,579; S. African Pat. No. 79 00 176). Numerous analogues of carbaprostacyclin are described (U.S. Pat. No. 4,306,076; Ger. Offen. No. 3,146,278; Ger. Offen. No. 3,204,443; *Prost. Leuko. Med.*, 9:307, 1982; *J. Org. Chem.* 48, 5341, 1983; *Tetrahedron Lett.* 3493, 1983; *Biochem. Pharmacol.* 32:2405, 1983; *Prost. Leuko. Med.* 11:391, 1983).

Synthetic prostaglandins (homo PGE$_2$ and homo PGF$_{2\alpha}$) have been prepared with the hydroxyl function and lower side chain trans-opposed in a 6-membered ring (*Tetrahedron Lett.*, 3327, 1971).

SUMMARY OF THE INVENTION

One aspect of the present invention relates to compounds of the formulas (1), (2) and (3):

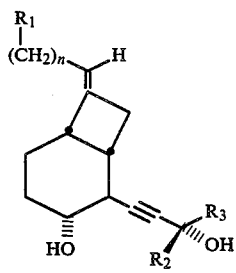
(1)

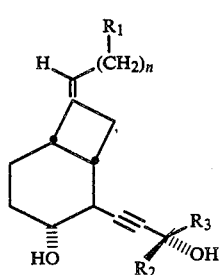
(2)

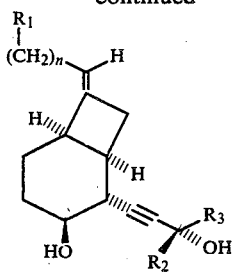
(3)

wherein:
n is 2 or 3;
R$_1$ is CH$_2$OH, CHO, CO$_2$R or CO$_2$H;
R$_2$ is hydrogen or methyl; and
R$_3$ is linear or branched alkyl having 5–10 carbon atoms,

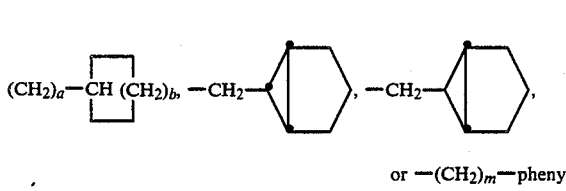

or —(CH$_2$)$_m$—phenyl optionally substituted with lower alkyl, lower alkoxy, trifluoromethyl, or halogen,
in which
a is 0, 1 or 2;
b is 3–7;
m is 1 or 2; and
R is

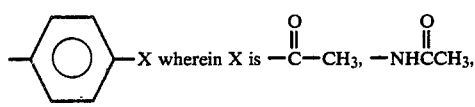

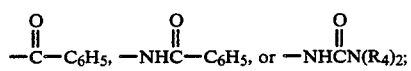

in which each R$_4$ is independently hydrogen, or lower alkyl having 1–6 carbon atoms,
and the pharmaceutically acceptable, non-toxic salts and esters thereof.

Another aspect of this invention is a method of treating cardiovascular disorders in mammals by administering a therapeutically effective amount of a compound of formula (1), (2), or (3) or a pharmaceutically acceptable salt or ester thereof.

Yet another aspect of the invention is a pharmaceutical composition containing at least one suitable pharmaceutical excipient and a compound of formula (1), (2), (3), or a pharmaceutically acceptable salt and ester thereof.

Lastly, another aspect of the invention is a process for preparing compounds of formulas (1), (2), (3), and their corresponding pharmaceutically acceptable, non-toxic salts and esters, as discussed below.

DETAILED DESCRIPTION OF THE INVENTION

Definitions

As used herein, the pharmaceutically acceptable, non-toxic salts of the compounds of formula (1), (2), (3), are carboxylic acid salts obtained by reaction of the COOH moiety in formula (1), (2) or (3) with a suitable amine or inorganic base. Specific preparations are discussed hereinafter.

The pharmaceutically acceptable carboxylic esters corresponding to the acids of formula (1), (2), (3), are prepared by conventional methods from the acid, e.g. by reaction with the appropriate diazoalkane, or an activated derivative optionally employing a condensing agent such as dicyclohexyl carbodiimide, by reaction of a salt with an appropriate active alkylating agent, or by ester exchange from an existing ester. Specific preparations are described in the procedures and examples below.

The term "alkyl" refers to and includes saturated branched and straight chain hydrocarbon radicals containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

"Cycloalkyl" as used herein means a saturated monocyclic hydrocarbon radical containing 3-8 carbon atoms, such as cyclopropyl, cyclobutyl, cyclopentyl, cyclohexyl, cycloheptyl and cyclooctyl.

The term, "lower alkyl" refers to a branched or unbranched saturated hydrocarbon chain of 1-4 carbons, such as, for example, methyl, ethyl, n-propyl, i-butyl and the like.

The term "alkoxy" refers to the radical —O-alkyl wherein "alkyl" is as defined above. This includes radicals such as methoxy, ethoxy, 2-propoxy, butoxy, 3-pentoxy and the like.

"Lower alkoxy" means the group —OR wherein R is lower alkyl as herein defined.

"Halo" as used herein denotes fluorine, chlorine, bromine, or iodine.

"Phenyl" as used herein encompasses all possible isomeric phenyl radicals optionally monosubstituted with a substituent selected from the group consisting of lower alkyl, lower alkoxy, hydroxy, trifluoromethyl and halogen.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The numbering system for the bicyclo[4.2.0]octane system shown in the scheme illustration below is used in naming the intermediates and product compounds of the invention.

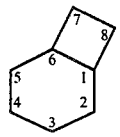

The absolute stereochemistry at carbons 1,2,3 and 6, and 3' of the side chain R attached to carbon 2 are specified according to the Cahn-Ingold-Prolog R-S system. When the compound is a pure enantiomer, the stereochemistry at each chiral carbon is specified by either R or S. When a compound is a racemic mixture the stereochemistry at each chiral carbon is specified by either R* or S* by reference to a single enantiomer of the racemate. In this manner relative stereochemistry is conveyed unambiguously, and the racemic modification is denoted by the asterisk "*". Olefin stereochemistry is specified by the IUPAC E-Z system. Classical nomenclature is used to name a compound having a triple bond as alkynyl; and two bonds emanating from the same atom as -ylidene. Exemplary names are given in the "Preferred Embodiments" section of this application.

PREFERRED EMBODIMENTS OF THE INVENTION

One preferred subclass of compounds of the invention includes compounds of formula (1), (2) and (3) wherein n is 2. Another preferred subclass are compounds of the invention in which $R_2$ is hydrogen. Yet another preferred subclass includes compounds in which $R_1$ is CHO, $CO_2R$ or $CO_2H$, particularly $CO_2R$ and $CO_2H$, and most particularly $CO_2H$. Still another preferred subclass includes compounds of the invention wherein $R_3$ is linear or branched alkyl having 5-10, preferably 5 or 7, and most preferably 5 carbon atoms,

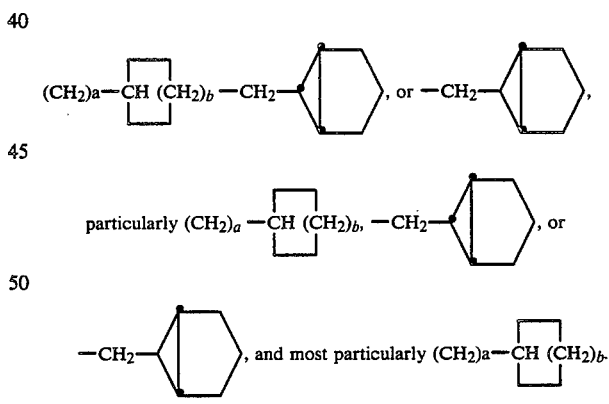

Yet another preferred subclass includes compounds of formulas (1), (2) and (3) in which n is 2 or 3, $R_1$ is $CO_2H$, $CO_2R$ or CHO; $R_2$ is hydrogen or methyl; and $R_3$ is linear or branched alkyl of 5 to 10 carbons,

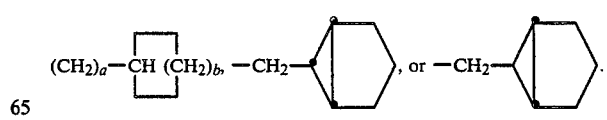

Within this subclass, a preferred group are compounds of formula (1), (2) and (3) in which n is 2 or 3, $R_1$ is CHO, $CO_2R$ or $CO_2H$, $R_2$ is hydrogen or methyl, and $R^3$ is linear or branched alkyl of 5 or 7 carbon atoms,

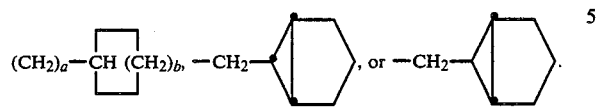

Among these, an especially preferred group are compounds of the invention wherein n is 2 or 3, $R_1$ is $CO_2R$ or $CO_2H$, $R_2$ is hydrogen or methyl, and $R_3$ is n-pentyl, or

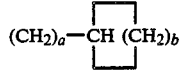

A particularly preferred subgroup are compounds of formulas (1), (2) and (3) in which n is 2, $R_1$ is $CO_2H$, $R_2$ is hydrogen, and $R_3$ is $(CH_2)_a$—CH $(CH_2)_b$ wherein a is 0 or 1 and b is 3–7, preferably 4 or 5, and most preferably 5; and the pharmaceutically acceptable, non-toxic salts and esters thereof. A most particularly preferred subgroup are those represented by formula (1) wherein $R_1$ is $CO_2H$; $R_2$ is H; $R_3$ is cyclohexyl. The foregoing statement of the preferred embodiments of the invention includes the pharmaceutically acceptable salts and esters, as well as the free bases of the compounds referred to above or named below.

At the present time, the most preferred compounds of this invention are:

(Z)-(3'S,1S,2S,3R,6S)-4-[2-(3'-hydroxy-3'-cyclohexyl-prop-1'-ynyl)-3-hydroxybicyclo[4.2.0]oct-7-ylidene]-butyric acid.

(Z)-3'S,1S,2S,3R,6S)-4-[2-(3'-hydroxy-3'-cyclopentyl-prop-1'-ynyl)-3-hydroxybicyclo[4.2.0]oct-7-ylidene]-butyric acid;

(Z)-(3'S*,1S*,2S*,3R*, 6S*)-4-[2-(3'-hydroxy-3'-cyclohexylprop-1'-ynyl)-3-hydroxybicyclo[4.2.0]oct-7-ylidene]butyric acid.

(Z)-(3'S*,1S*,2S*,3R*,6S*)-4-[2-(3'-hydroxy-3'-cyclopentylprop-1'-ynyl)-3-hydroxybicyclo[4.2.-0]oct-7-ylidene]butyric acid;

and the pharmaceutically acceptable, non-toxic salts and esters thereof.

PREPARATION PROCEDURES

I. Compounds wherein $R_1$ is $CO_2H$.

Compounds of formulas (1), (2), or (3) wherein $R_1$ is $CO_2H$ are prepared according to Reaction Scheme I. In the detailed description, the Roman numerals in parentheses correspond to the compound shown in the reaction scheme.

Scheme I

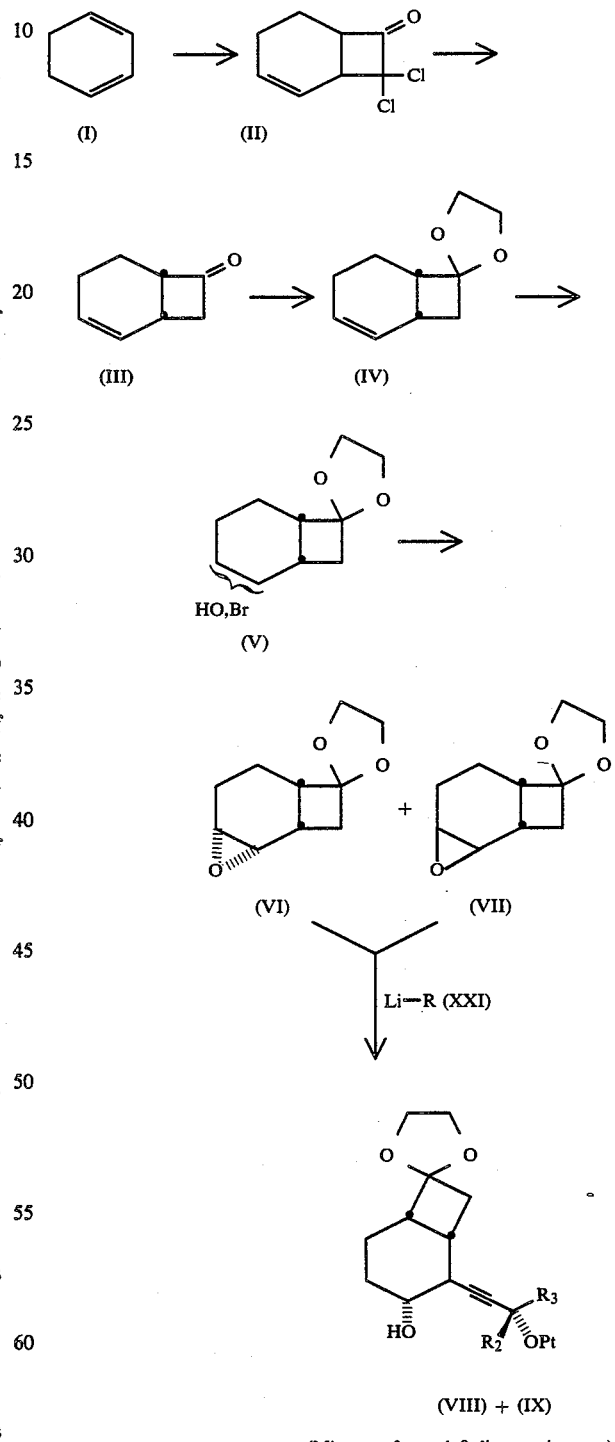

(VIII) + (IX)

(Mixture of α and β diastereoisomers)

-continued
Scheme I

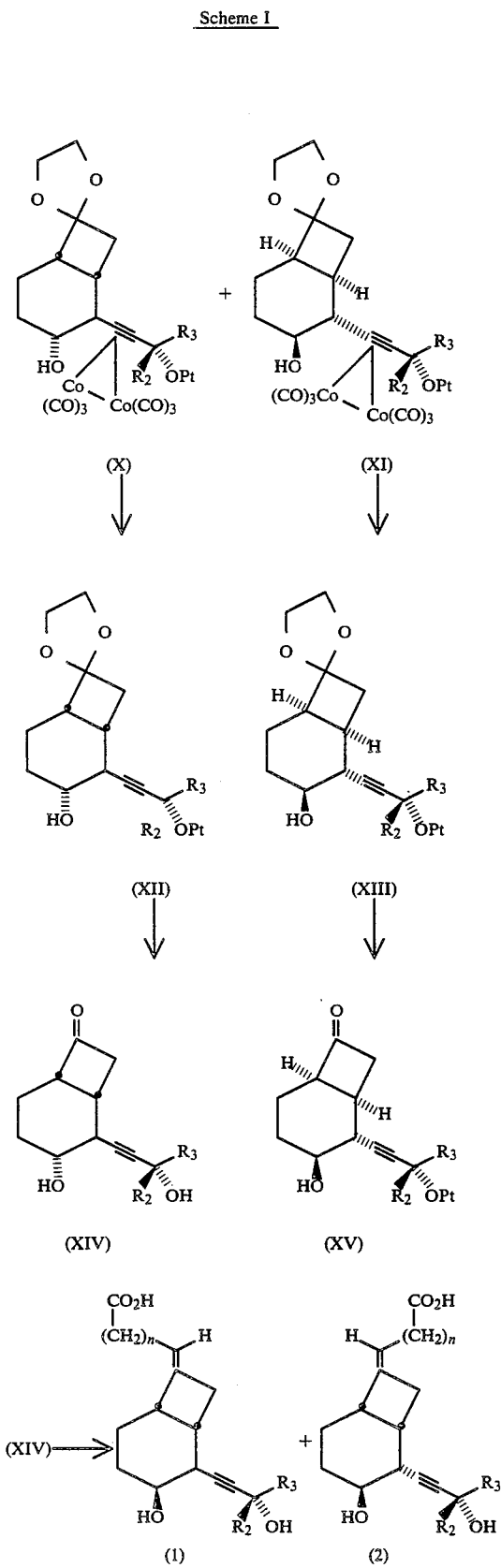

-continued
Scheme I

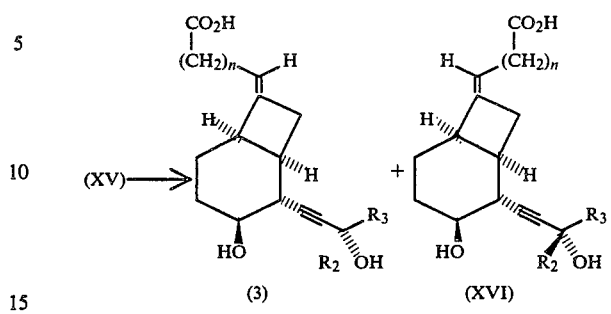

The synthesis of the compounds of formulas (1), (2), and (3) begins with reaction of 1,3-cyclohexadiene (I) with dichloroacetyl chloride forming 8,8-dichlorobicyclo-[4.2.0]oct-2-en-7-one (II), which, when reacted with tributyltin hydride, results in formation of bicyclo[4.2.0]oct-2-en-7-one (III) (*Tetrahedron*, 27:615, 1971).

Bicyclo[4.2.0]oct-2-en-7-one is reacted with ethylene glycol to give the acetyl (IV). The acetal is subsequently reacted with N-bromoacetamide and water in acetone to give a mixture of bromohydrins (V), which are converted to a mixture of epoxy acetals (VI) and (VII) upon treatment with potassium carbonate.

The bicyclic epoxy acetals (VI) and (VII) can be reacted with an organolithium reagent of general structure Li-R (XXI) in the presence of boron trifluoride etherate to give the diastereomeric alcohols, VIII and IX, where

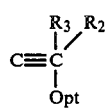

in which $R_2$ and $R_3$ are as previously defined and Pt is a protecting group for the side chain hydroxyl function.

Preparation of the organolithium reagents of formula XXI is discribed following Reaction Scheme II, below. Suitable protecting groups include, but are not limited to, silyl ethers, tertiary alkyl ethers, e.g. tert-butyl, (optionally substituted) triphenylmethyl ethers, acetals such as tetrahydropyranyl ethers, and the like. Usually trialkyl silyl ethers are preferred, and particularly preferred are the tert-butyldimethylsilyl derivatives. These ethers are prepared from the corresponding carbinols by standard procedures well known to those skilled in the art; the tert-butyldimethylsilyl ethers, in particular, are used extensively in prostaglandin chemistry and can be conveniently prepared by reaction of the appropriate carbinol with tert-butyldimethylsilyl chloride in N,N-dimethylformamide solution in the presence of imidazole, which functions in the dual capacities of specific catalyst for the silylation and as base, to neutralize the hydrochloric acid which constitutes the other reaction product.

Organolithium reagents of the alkynyl type are prepared from the corresponding 1-alkyn-3-ols, which in turn can be readily obtained by reaction of an acetylenic Grignard reagent, i.e. ethynyl magnesium halide, or lithium acetylide, with aldehydes (R) or ketones ($R_2R_3C=O$), furnishing ethynyl carbinols

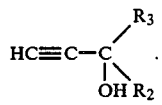

(Preparation of 1-alkyn-3-ols is described in greater detail in Preparation 3.A.)Protection of the hydroxyl moiety with a suitable protecting group, such as are described above, gives the corresponding ethers

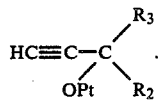

Conversion to an organolithium reagent can be effected, usually by exchange reaction with a stoichiometric quantity of a more reactive organolithium species, e.g. an alkyl lithium reagent RLi, to give the acetylenic lithium reagent

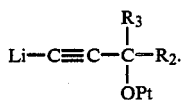

In the reaction of the lithium acetylenic reagent with the mixture of epoxyacetals VI and VII, only the alpha epoxide VI undergoes reaction. In this reaction the attack by the lithium acetylide reagent occurs regioselectively at position 2 of compound VI to give a mixture of diastereoisomers VIII and IX. For example, reaction of VI and VII with (S)-1-lithio-3-(tert-butyldimethylsilyloxy)-3-cyclohexylprop-1-yne in the presence of boron trifluoride etherate furnishes a mixture of the diastereoisomeric carbinols VIII—(3′S,1R,2S,3R,6S)-spiro[2-(3′-tert-butyldimethylsilyloxy)3′-cyclohexylprop-1′-ynyl)-3-hydroxybicyclo[4.2.0]octane-7,2′-[1.3]dioxolan]; and IX—(3′S,1S,2R,3S,6R)-spiro[2-(3′-tert-butyldimethylsilyloxy)3′-cyclohexylprop-1′-ynyl)-3-hydroxybicyclo[4.2.0]octane-7,2′-[1.3]dioxolan].

The mixture of diastereomeric bicyclo[4.2.0]octanols VIII and IX is converted into a mixture of the dicobalt hexacarbonyl complexes X and XI by reaction with dicobaltoctacarbonyl in diethylether. These complexes are separated chromotographically to give the separate complexes X and XI, which are each reacted with ceric ammonium nitrate to give the compounds of formulas XII and XIII, for example (3′S,1R,2S,3R,6S)-spiro[2-(3′-tert-butyldimethylsilyloxy-3′-cyclohexylprop-1′-ynyl)-3-hydroxybicyclo[4.2.0]octan-7,2′-[1.3]dioxolan] (XII), and (3′S,1S,2R,3S,6R)-spiro[2-(3′-tert-butyldimethylsilyloxy-3′-cyclohexylprop-1′-ynyl)-3-hydroxybicyclo[4.2.0]octan-7,2′-[1.3]dioxolan] (XIII), respectively. These are each reacted with dilute sulfuric acid to effect acetal hydrolysis and also hydrolysis of the silyl protective group to give the compounds of formulas XIV and XV, for example (3′S,1R,2S,3R,6S)-2-(3′-hydroxy-3′-cyclohexylprop-1′-ynyl)-3-hydroxybicyclo[4.2.0]octan-7-one (XIV), and (3′S,1S,2R,3S,6R)-2-(3′-hydroxy-3′-cyclohexylprop-1′-ynyl)-3-hydroxybicyclo[4.2.0]octan-7-one (XV), respectively.

For the preparation of the triphenylphosphorane ylids used for the Wittig reactions that convert XIV and XV to (1), (2), and (3), the corresponding triphenylphosphonium salts are deprotonated with two equivalents of dimsyl sodium in dimethyl sulfoxide. The triphenylphosphonium salts are prepared by condensing triphenylphosphine with an Ω-halocarboxylic acid as described in *J. Org. Chem.* 27, 3404 (1962). The crude phosphonium salts are purified typically by washing with diethyl ether or by recrystalization from acetonitrile or ethanol-diethyl ether.

The bicyclooctanone alkynol of formula XIV is then reacted with an appropriately chosen triphenylphosphorane ylid having a 4 to 5 carbon atom chain length to yield a mixture of the Z and E alkanoic acids (1) and (2), for example Z-and E-(3′S,1S,2S,3R,6S)-2-(3′-hydroxy-3′-cyclohexylprop-1-ynyl)-3-hydroxybicyclo[4.2.0]oct-7-ylidene. This mixture is separated chromatographically to give, for example, Z-(3′S,1S,2S,3R,6S)-2-(3′-hydroxy-3′-cyclohexylprop-1′-ynyl)-3-hydroxybicyclo[4.2.0]-oct-7-ylidenealkanoic acid (1) and E-(3′S,1S,2S,3R,6S)-2-(3′-hydroxy-3′-cyclohexylprop-1′-ynyl)-3-hydroxy bicyclo[4.2.0]oct-7-ylidenealkanoic acid (2). Similarly, the bicyclooctanon alkynol of formula XV is reacted with an appropriate triphenylphosphorane ylid having a 4 to 5 carbon atom chain length to give a mixture of Z and E alkanoic acids (3) and XVI. This mixture is separated chromatographically to give, for example, Z-(3′S,1R,2R,3S,6R)-2-(3′-hydroxy-3′-cyclohexylprop-1-ynyl)-3-hydroxybicyclo[4.2.0]oct-7-ylidene alkanoic acid (3) and E-(3′S,1R,2R,3S,6R)-2-(3′-hydroxy-3′-cyclohexylprop-1′-ynyl)-3-hydroxybicyclo[4.2.0]oct-7-ylidene alkanoic acid XVI.

The structures depicted herein, including the novel compounds of our invention, have multiple chiral centers and are optically active. While, for illustrative purposes, only one optical isomer is depicted, our invention encompasses all optical isomers and mixtures thereof, said mixtures including racemates and diastereomeric mixtures in all proportions. If the product compounds of our invention are prepared from optically inactive starting materials and without employment of chiral reagents, the products will be obtained as (optically inactive) racemic mixtures.

The optically active acetylenes used in Scheme I in which $R_2$ is hydrogen are prepared according to Scheme II.

Scheme II

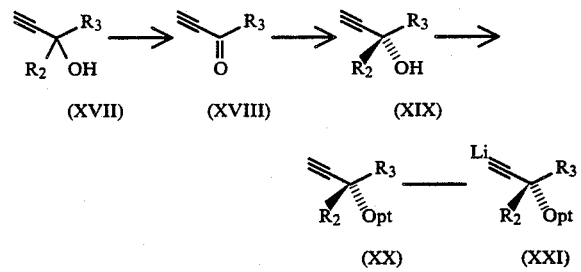

As shown in Scheme II a propargylic alcohol of formula XVII, wherein $R_2$ is H, is oxidized with Jones reagent to give a propargylic ketone of formula XVIII. This ketone is reduced with isopinocamphenyl-9-borabicyclo[3.3.1]nonane according to the method described in J.Amer.Chem.Soc., 101, 2352 (1979) to give the chiral propargylic alcohols (XIX). The propargylic alcohols XIX are converted into O-protected derivatives XX by condensation with trialkylsilyl chlorides and imidazole. Compounds XX are reacted with butyllithium to give lithioacetylides XXI, which are used in Scheme I to convert epoxide VI into VIII and XI. Propargylic alcohols of formula XVII wherein $R_2$ is methyl are prepared according to the general method of *Organic Synthesis,* Collective Volume 3, page 320 (1955).

The optically alctive acetylenes used in Scheme I wherein $R_2$ is H or $CH_3$ may also be prepared according to Scheme III. Scheme III is the method of Fried (*Ann.-N.Y.Acad.Sci.*, 180, 39 (1971)). In this method a hemiphthalate of racemic XVII, which is formed by condensation of XVII with phthalic anhydride, is converted into a mixture of diastereoisomeric salts XXII and XXIII using a suitable optically active amine. The mixture of salts is recrystallized from an appropriate solvent, typically acetonitrile, to give a pure diastereoisomeric salt XXII. This salt is treated with dilute aqueous hydrochloric acid to give hemiphthalate XXIV, which is hydrolyzed with aqueous base to give chiral acetylenic alcohol XXV.

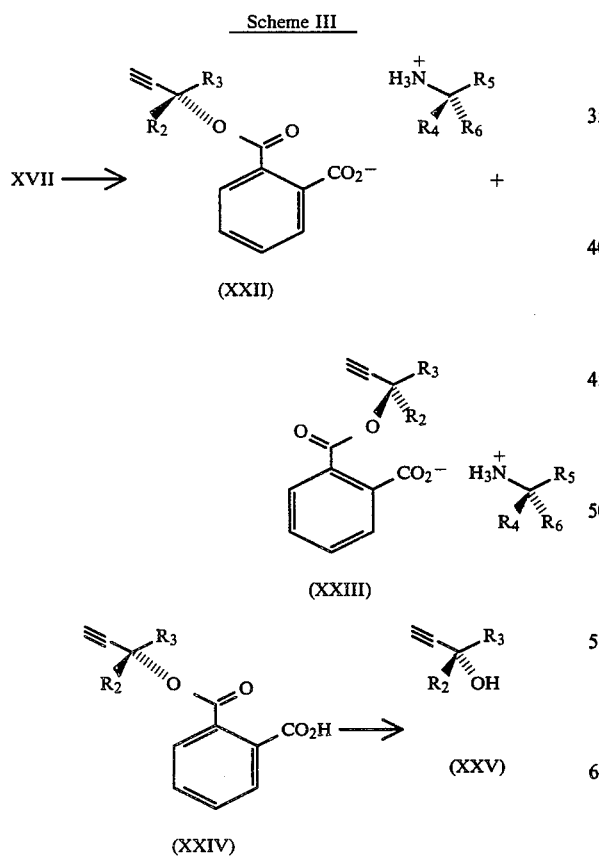

An alternative method for preparing the chiral intermediates of Scheme I using racemic intermediates is described in Scheme IV.

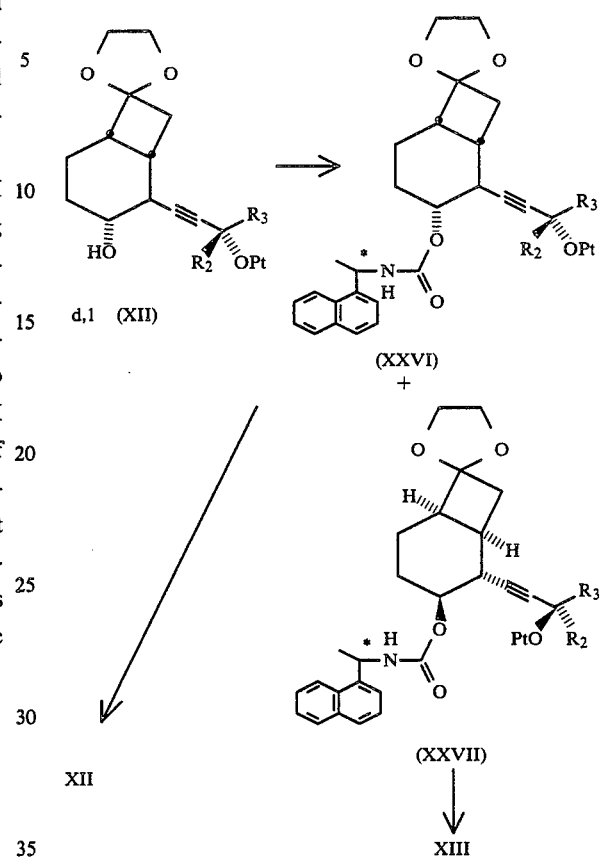

Condensation of racemic intermediate XII with (R)-(−)-α-naphthylethylisocyanate gives a mixture of diastereoisomers XXVI and XXVII. These are separated by chromatography to give the individual diastereoisomers XXVI and XXVII. Compounds XXVI and XXVII are reacted individually with lithium aluminum hydride to give enantiomers XII and XIII respectively.

The pharmaceutically acceptable non-toxic salt derivatives of the compounds of formula (1), (2), (3) are prepared by treating the free acids with an appropriate amount of pharmaceutically acceptable base. Representative pharmacetically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, procaine, choline, betaine, ethylenediamine, glucosamine, methylglucamine, theobromine, purines, piperazine, piperidine, N-ethylpiperidine, polyamine resins and the like. For preparing, for example, monovalent cation salts, the free acid starting material of formula (1), (2), or (3) is treated with one molar equivalent of pharmaceutically acceptable base in an appropriate solvent such as water, methanol, ethanol, isopropanol, butanol, acetone, dioxane or tetrahydrofuran. The molar ratio of compounds of formula (1), (2), or (3) to base used are chosen to provide the ratio desired for any particular salt. For preparing, for example, divalent cation salts such as the calcium or magnesium salts the free acid starting material of formula (1), (2) or (3) is treated with at least one-half molar equivalent of pharmaceutically acceptable base to yield a neutral salt. Similarly, for the trivalent cation aluminum salts, at least one-third molar equivalent of the aluminum base is employed if a neutral salt product is desired.

The novel free carboxylic acids (1), (2) and (3) of our invention can be reliberated from their respective salts by treating said salts with at least stoichiometric quantities of a strong acid, preferably an inorganic acid, e.g., hydrochloric acid, sulfuric acid, and the like, at temperatures ranging from about 0° C. to about 50° C., preferably at room temperature.

The pharmaceutically acceptable non-toxic esters of the novel acids (1), (2), and (3) of our invention can be prepared, e.g. by esterifying the corresponding free acids with a solution of the appropriate diazoalkane in a suitable inert solvent such as diethyl ether. An alternative and general method for producing the esterified acids of our invention comprises reaction of a benzene solution of the carboxylic acid with an alkyl halide in the presence of the organic base diazabicycloundecane (DBU) at temperatures from about 20° C.-80° C., and for about 1-12 hours. These conditions are particularly useful for esterifying acids containing labile functionality in the molecule, such as the prostaglandins and their synthetic analogues, since they avoid the use of acid catalysts and in fact involve no harsh reagents. (N. Ono et al, *Bull.Chem.Soc.Japan*, 51, 2401–2404 (1978)).

Typical esters are those esters derived from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, catalyzed by the corresponding alkoxide according to methods known in the art. It is preferred in preparing the esters via transesterification to go from a lower ester to a higher ester, e.g., from the methyl ester to the isoamyl ester. However, by using a substantial excess of a lower alcohol, a higher ester can be transesterified to a lower ester; thus, for example, by using a substantial excess of ethanol, the hexyl ester is converted by transesterification to the ethyl ester.

Salts of the compounds of formula (1), (2), and (3) may be interchanged by taking advantage of differential solubilities of the salts volatilities or activities of the acids, or by treating with the appropriately loaded ion exchange resin. For example, the interchange is effected by the reaction of a salt of the compounds of formula (1), (2), and (3) with a slight stoichiometric excess of an acid of a lower pKa than the acid component of the starting salt. This conversion is carried out at a temperature between about 0° C. and the boiling point of the solvent being used as the medium for the procedure.

II. Compounds Wherein $R_1$ is $CH_2OH$ or CHO

Compounds of formulas (1), (2), or (3) wherein $R_1$ is $CH_2OH$ or CHO are prepared from the corresponding compounds (1), (2), or (3) wherein $R_1$ is $CO_2H$, according to Scheme V. Scheme V demonstrates a method for the conversion of (1) wherein $R_1$ is $CO_2H$ into (1) wherein $R_1$ is $CH_2OH$ or CHO. By appropriate substitution of (1) wherein $R_1$ is $CO_2H$ the reactions of Scheme V may be used to prepare (2) or (3) wherein $R_1$ is $CH_2OH$ or CHO.

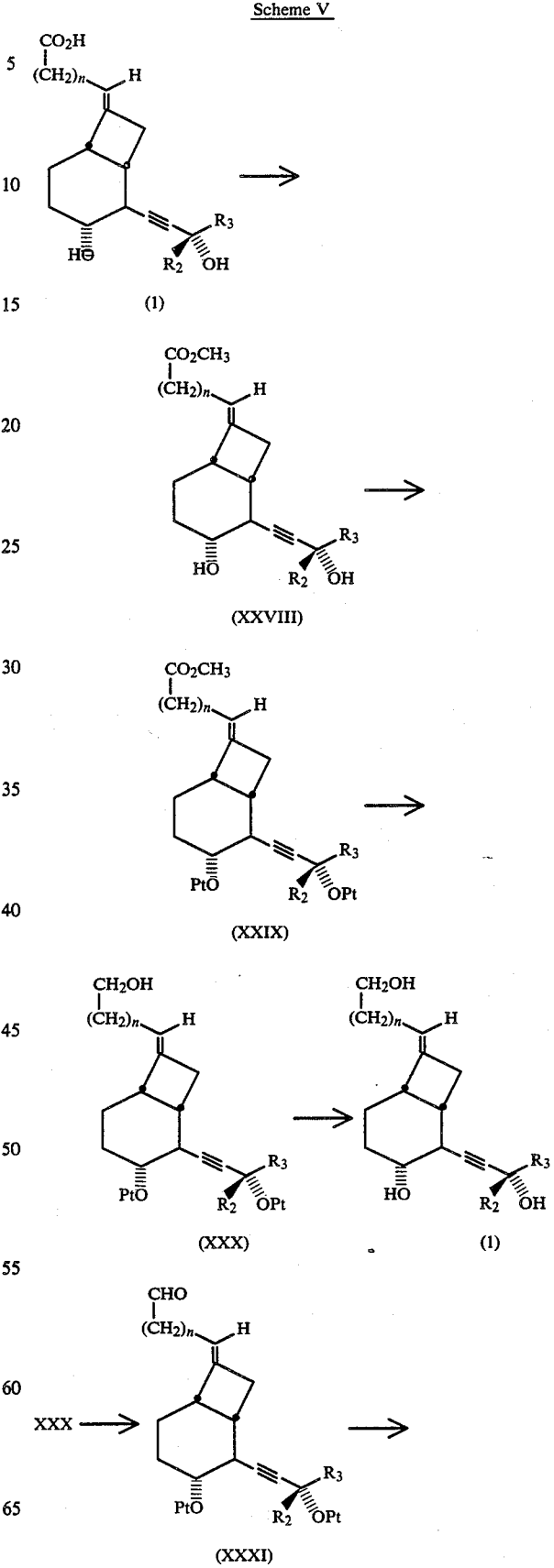

Scheme V

-continued
Scheme V

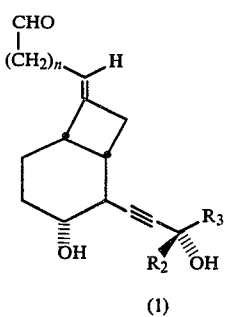

(1)

For example, reaction of (1) wherein $R_1$ is $CO_2H$ with diaziomethane gives the methyl ester XXVIII. Reaction of XXVIII with excess tert-butyldimethylchlorosilane in the presence of triethylamine and 4-dimethylaminopyridine gives the bis-protected derivative XXIX ($Pt=Si(CH_3)_2t$-Bu). Reduction of XXIX with lithium aluminum hydride gives carbinol XXX, which is converted to (1) wherein $R_1$ is $CH_2OH$ by reaction with tetrabutylammonium fluoride in tetrahydrofuran. Oxidation of XXX with pyridinium chlorochromate gives aldehyde XXXI, which is converted into (1) wherein $R_1$ is CHO by reaction with tetrabutylammonium fluoride in tetrahydrofuran.

III. Compounds Wherein $R_1$ is $CO_2R$

Compounds (1), (2), or (3) wherein $R_1$ is $CO_2R$ are prepared according to Scheme VI.

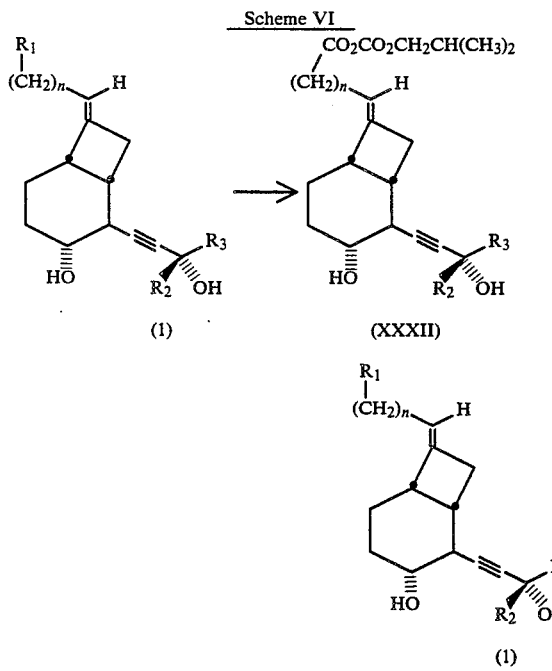

Scheme VI demonstrates a method for conversion of (1) wherein $R_1$ is $CO_2H$ into (1) wherein $R_1$ is $CO_2R$. By appropriate substitution of (1) wherein $R_1$ is $CO_2H$ by either (2) or (3) wherein $R_1$ is $CO_2H$ the reactions of Scheme VI may be used to prepare (2) or (3) wherein $R_1$ is $CO_2R$. In this method a compound of formula (1), (2) or (3) wherein $R_1$ is $CO_2H$ is condensed with isobutyl chlorocarbonate to give an anhydride represented in the case of (1) by formula XXXII, Compound XXXII is reacted with a substituted phenol to give compounds (1) wherein $R_1$ is $CO_2R$. The phenols used in this Scheme are known in the prior art and their application to the preparation of phenyl esters is described in *J. Pharm. Sci.* 68,833 (1979).

UTILITY AND ADMINISTRATION

The compounds of the present invention are useful for the treatment of cardiovascular disorders; in particular they are vasodilaters, and inhibit accumulation of cholesterol in the vascular wall and in plasma. They are also potent inhibitors of the aggregation of platelets and the release from them of pro-coagulant and pro-atherosclerotic factors. Accordingly, these compounds are useful in treating and preventing cardiovascular disorders involving atherosclerosis, thrombotic and vasopastic conditions. They also are useful antihypertensive and cholesterol lowering agents.

The compounds of this invention display the spectrum of activities associated with prostacyclin. However, in contrast to prostacyclin, whose therapeutic potential is severely compromised by its extreme chemical instability, the compounds of our invention retain high biological activity while displaying much greater chemical stability, a combination of attributes identifying them as promising agents for prophylactic and/or therapeutic use particularly in the treatment of cardiovascular dysfunction and disease. Many of these compounds are selective in their antithrombotic effect, and they achieve this therapeutic effect without substantially affecting blood pressure.

Administration of the active compounds in the pharmaceutical composition described hereinafter can be via any of the accepted modes of administration for agents which affect the cardiovascular system. These methods include oral, parenteral, topical and otherwise systemic administration. Depending on the intended mode, the composition may be in the form of solid, semi-solid or liquid dosage forms, such as, for example, tablets, suppositories, pills, capsules, powders, liquids, suspension, or the like, preferably in unit dosage forms suitable for single administration of precise dosages. The composition will include a conventional pharmaceutical carrier or excipient and an active compound of formula (1), (2), or (3) and/or the pharmaceutically acceptable salts thereof and, in addition, may include other medicinal agents, pharmaceutical agents, carriers, adjuvants, etc.

The present invention further relates to a method for treating cardiovascular disorders in mammals, which method comprises administering to a subject in need thereof an effective amount of a compound selected from those represented by formulas (1), (2), (3) or their pharmaceutically acceptable non-toxic salts or esters, or a pharmaceutical composition incorporating such compound(s) as an active ingredient.

The present invention still further relates to pharmaceutical compositions useful for treating cardiovascular disorders. These compositions comprise an effective amount of a compound selected from those represented by formulas (1), (2) and (3) or their pharmaceutically acceptable non-toxic salts or esters in acceptable, non-toxic carrier.

The amount of active compound administered will of course, be dependent on the subject being treated, the severity of the affliction, the manner of administration and the judgment of the prescribing physician. However, an effective dosage will be in the range of 0.001–15 mg/kg/day, preferably 0.01–3 mg/kg/day. For an average 70 kg human, this would amount to 0.07–1000 mg per day, or preferably 0.7–210 mg/day.

The novel compounds of this invention may be formulated with suitable pharmaceutical vehicles known in the art to form particularly effective cardiovascular compositions. Generally, an effective amount of active ingredient is about 0.001% w to about 10% w of the total formulated composition. The rest of the formulated composition will be about 90% w to about 99.999% w of a suitable excipient.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.5%–10%; preferably 1–2%.

The following Preparations and Examples serve to illustrate the invention and make the invention enabling. They should not be construed as narrowing it or limiting its scope in any way.

PREPARATION 1

Preparation of Spiro[bicyclo[4.2.0]oct-2-ene-7,2'-[1.3]dioxolan], and Related Compounds of Formula IV A mixture of 6.4 g bicyclo[4.2.0]oct-2-en-7-one (III), (Tetrahedron, 27, 615 (1971)), 18.62 g ethylene glycol, 100 ml benzene, and 25 mg p-toluenesulfonic acid is heated at reflux for 4 hr using a Dean-Stark trap to effect continuous removal of water. The cooled reaction mixture is poured onto 100 ml saturated sodium bicarbonate solution and the resulting mixture is extracted with three 75 ml portions of diethyl ether. The combined organic extract is washed with 100 ml saturated sodium chloride solution and is then dried over sodium sulfate. The solvent is removed under vacuum and the residue is distilled under vacuum to give 7.12 g of spiro[bicyclo[4.2.0]oct-2-ene-7,2'-[1.3]dioxolan] (IV).

PREPARATION 2

Preparation of (1S*,2S*,4R*,7S*)-Spiro[3-Oxatricyclo[5.2.0.0$^{2,4}$]nonane-8,2'-[2.3]dioxolan], (1S*,2R*,4S*,7S*)-Spiro[3-oxatricyclo[5.2.0.0$^{2,4}$]nonane-8,2'-[1.3]dioxolan], and Related Compounds of formulas VI and VII To a stirred solution of 5 g of spiro[bicyclo[4.2.0]oct-2-ene-7,2'-[1.3]dioxolan], prepared according to Preparation 1, in 40 ml acetone and 20 ml water at 0° C. is added 4.76 g of N-bromacetamide over 1 hr. This mixture is stirred at room temperature for 20 hr. To this solution is added 12.4 g potassium carbonate and the resulting mixture is stirred at room temperature for 3 days. The mixture is saturated with sodium chloride and the resulting mixture is extracted with four 150 ml portions of diethyl ether. The combined organic extract is washed with 100 ml of saturated sodium chloride solution and is dried over sodium sulfate. Removal of solvent in vacuum and chromatographic purification of the residue on silica gel eluting with 15% ethyl acetate-hexane gives 3.45 g of a ca. 4:1 mixture of (1S*,2S*,4R*,7S*)-spiro[3-oxatricyclo[5.2.0.0$^{2,4}$]nonane-8,2'-[1.3]dioxolan] VI and (1S*,2R*,4S*,7S*)-spiro[3-oxatricyclo[5.2.0.0$^{2,4}$]nonane-8,2'-[1.3]dioxolan] VII.

PREPARATION 3

Preparation of 3-OH-1-Alkynes of Formula XVII

A. A rapid stream of acetylene was passed through a solution of 2M methyl magnesium bromide (100 ml) in THF until no more methane evolution was observed. 10 g of hexanal was added at 0° C., stirred for ½ h and a saturated solution of NH$_4$Cl was added. The organic product was isolated by extraction with ether. The ether solution was washed with water, brine, dried over MgSO$_4$ and evaporated to give a liquid, which was purified by distillation, to give 3-hydroxyoct-1-yne.

B. Similarly, the following representative compounds of Formula XVII are prepared:
3-cyclohexylpropyl-1-yn-3-ol;
1-decyn-3-ol;
1-tridecyn-3-ol;
(R)-5-methyl-1-nonyn-3-ol;
1-nonyn-3-ol;
4-phenyl-1-butyn-3-ol;
5-phenyl-1-pentyn-3-ol;
3-methyl-4-phenyl-1-butyn-3-ol;

4-m-trifluoromethylphenyl-1-butyn-3-ol;
4-endo-bicyclo[3.1.0]hex-6-yl-1-butyn-3-ol;
4-exo-bicyclo[3.1.0]hex-6-yl-1-butyn-3-ol;
3-methyl-3-cyclobutyl-1-propyn-3-ol;
3-methyl-3-cyclopentyl-1-propyn-3-ol;
3-cyclopentyl-1-propyn-3-ol;
4-cyclopentyl-1-butyn-3-ol, and
4-cyclohexyl-1-butyn-3-ol.

PREPARATION 4

Preparation of 1-Cyclohexyl-2-propyn-1-one and Related Compounds of Formula XVIII A. A solution of chromic acid was prepared by dissolving 106.88 g chromium trioxide in 400 ml water and then adding 92 ml concentrated sulfuric acid. This solution is added in dropwise fashion over a 3 hr. period to an ice cooled, stirred solution of 120 g 3-cyclohexyl-1-propyn-3-ol in 175 ml acetone. The resulting mixture was diluted with 500 ml water and the product was extracted into 1 liter of diethyl ether. The ether extract was washed with 250 ml saturated sodium bisulfite solution and was dried over sodium sulfate. The diethyl ether was removed by distillation under nitrogen atmosphere and the resulting residue was purified by Kugelrohr distillation (65° C., 0.1 mm Hg) to give 84.9 g of 1-cyclohexyl-2-propyn-1-one as an oil: MS m/z=136 (M+) Calcd. for $C_9H_{12}O$:C, 79.37; H, 8.88. Found:C, 79.24; H, 8.6.

B. In like manner, but replacing the 3-cyclohexyl-1-propyn-3-ol with 1-octyn-3-ol, 1-octyn-3-one was prepared.

C. Similarly, but starting with other appropriate compounds of Formula XVII, prepared in accordance with Preparation 3.B., the following compounds of Formula XVIII are prepared:
1-decyn-3-one;
1-tridecyn-3-one;
(R)-5-methyl-1-nonyn-3-one;
1-nonyn-3-one;
4-phenyl-1-butyn-3-one;
5-phenyl-1-pentyn-3-one;
4-m-trifluoromethylphenyl-1-butyn-3-one;
4-endo-bicyclo[3.1.0]hex-6-yl-1-butyn-3-one;
4-exo-bicyclo[3.1.0]hex-6-yl-1-butyn-3-one;
3-cyclopentyl-1-propyn-3-one;
4-cyclopentyl-1-butyn-3-one; and
4-cyclohexyl-1-butyn-3-one.

PREPARATION 5

Preparation of (S)-3-cyclohexyl-1-propyn-3-ol and Related Compounds of Formula LIX A mixture of 1.6 liters 0.5M 9-borabicyclo[3.3.1]nonane in tetrahydrofuran and 122.6 g (−)-α-pinene was heated at reflux under nitrogen for 4 hr., at which time the excess (−)-α-pinene and tetrahydrofuran were removed under vacuum to leave a thick oil. The contents of the flask were cooled to 0° C. and 80 g of 1-cyclohexyl-2-propyn-1-one, prepared according to Preparation 4, was added with stirring. The resulting mixture was allowed to warm to 23° C. and it was stirred at that temperature for 16 hr. Excess S-Alpine borane was destroyed by adding 44 ml propionaldehyde and stirring at 23° C. for 1 hr. The liberated (−)-α-pinene was removed by vacuum distillation. The resulting mixture was diluted with 400 ml tetrahydrofuran followed by 300 ml 3N sodium hydroxide. To this stirred mixture was added in dropwise fashion 300 ml 30% hydrogen peroxide over 1 hr. The mixture was heated at 40° C. for 3 hr. After cooling, the mixture was extracted with diethyl ether and this extract was dried over magnesium sulfate. Evaporation of the solvent and purification of the residue by silica gel flash chromatography using 5% ethyl acetate-hexane gave 56 g of (S)-3-cyclohexyl-1-propyn-3-ol, which by nmr analysis was shown to be 90% e.e.

Recrystallization from hexane gave 45 g of the pure S isomer, mp 56°–58°, $[\alpha]_D^{25} = -11.1°$ (C=0.53, Et$_2$O)

B. In like manner, but replacing the 1-cyclohexyl-2-propyn-1-one with 1-octyn-3-one, prepared as described in Preparation 4.B., we prepared (S)-1-octyn-3-ol; $[\alpha]_D^{25} = -39.7°$ (C=1, CHCl$_3$).

C. Similarly, but utilizing instead, other suitable compounds of Formula XVIII, prepared according to Preparation 4.C., the following compounds of Formula XIX are prepared:
(S)-1-decyn-3-ol;
(S)-1-tridecyn-3-ol;
(3S,5R)-5-methyl-1-nonyn-3-ol;
(S)-1-nonyn-3-ol;
(S)-4-phenyl-1-butyn-3-ol;
(S)-5-phenyl-1-pentyn-3-ol;
(S)-4-m-trifluoromethylphenyl-1-butyn-3-ol;
(S)-4-endo-bicyclo[3.1.0]hex-6-yl-1-butyn-3-ol;
(S)-4-exo-bicyclo[3.1.0]hex-6-yl-1-butyn-3-ol;
(S)-3-cyclopentyl-1-propyn-3-ol;
(S)-3-cyclooctyl-1-propyn-3-ol;
(S)-4-cyclopentyl-1-butyn-3-ol; and
(S)-4-cyclohexyl-1-butyn-3-ol.

PREPARATION 6

Preparation of (S)-3-cyclohexyl-1-propyn-3-ol and Related Compounds of Formula XXV A. A mixture of 50 g racemic 3-cyclohexyl-1-propyn-3-ol, prepared according to Preparation 3, 53.3 g phthalic anhydride, and 100 ml pyridine is heated at 90° C. for 4 hours. After cooling to 0° C. this mixture is added with stirring to a mixture of 350 ml concentrated hydrochloric acid and 900 ml ice. The oily solid that separated is dissolved in 600 ml diethyl ether. This solution is washed with saturated NaCl solution and is dried over sodium sulfate. Evaporation and recrystallization from acetone/hexane gives the hemi-phthalate, mp 136°–138° C. This hemi-phthalate (38.5 g) is suspended in 80 ml dichloromethane and a solution of 16.2 g (−)-α-phenylethylamine in 250 ml dichloromethane is added with stirring over 15 minutes. The mixture is filtered after 1 hour and the filtrate is evaporated to give a mixture of diastereoisomeric salts. This mixture is recrystallized five times from acetonitrile to give 7 g of a pure diastereoisomeric salt mp 142°–143° C., $[\alpha]_D = -36.7$ (C=1, CHCl$_3$). This salt (2 g) is added to a stirred mixture of 25 ml 5% sodium bicarbonate and 25 ml diethyl ether. The ether layer is discarded and the aqueous layer is extracted with 3 additional 25-ml portions of diethyl ether. The aqueous layer is acidified with 4N HCl and is extracted thoroughly with diethyl ether. The ether extract is dried over sodium sulfate and is evaporated to dryness to give 1.37 g (S)-3-cyclohexyl-prop-1-yn-3-ol, mp 70°–74° C., $[\alpha]_D = -35.8°$ (C=1, CHCl$_3$).

B. Similarly, but starting with other compounds of Formula XVII, prepared in accordance with Preparation 3.B., the following compounds of formula XXV are prepared;

(S)-1-octyn-3-ol;
(S)-1-decyn-3-ol;
(S)-1-tridecyn-3-ol;
(3S,5R)-5-methyl-1-nonyn-3-ol;
(S)-1-nonyn-3-ol;
(S)-4-phenyl-1-butyn-3-ol;
(S)-5-phenyl-1-pentyn-3-ol;
(S)-4-m-trifluoromethylphenyl-1-butyn-b 3-ol;
(S)-4-endo-bicyclo[3.1.0]hex-6-yl-1-butyn-3-ol;
(S)-4-exo-bicyclo[3.1.0]hex-6-yl-1-butyn-3-ol;
(S)-3-cyclopentyl-3-methyl-1-propyn-3-ol;
(S)-3-cyclobutyl-3-methyl-1-propyn-3-ol;
(S)-3-cyclooctyl-1-propyn-3-ol;
(S)-4-cyclopentyl-1-butyn-3-ol;
(S)-3-cyclopentyl-1-propyn-3-ol; and
(S)-4-cyclohexyl-1-butyn-3-ol.

PREPARATION 7

Preparation of 3-Tert-butyldimethylsilyoxyoct-1-yne and Related Silyl Ethers of Formula IX A. To a solution of (S)-3-cyclohexyl-1-propyn-3.ol, (obtained according to Preparation 5.A) (2.76 g, 0.02 mol), in 10 ml N,N-dimethylformamide (DMF), cooled to 0° C., was added imidazole (2.1 g), followed by tert-butyldimethylchlorosilane (3.1 g, 0.02 mol). The mixture was stirred for 3 h. Water (80 ml) and hexane (80 ml) were added; the organic layer was separated and combined with 2×80 ml of hexane extractions of the aqueous layer. The solvent was removed (in vacuo), after drying over sodium sulfate, to give a crude residue (4.3 g) which was chromatographed on silica gel (80 g), eluting with ethyl acetate-hexane (2:1, v/v) to afford 3-tert-butyldimethylsilyloxy-3-cyclohexylprop-1-yne.

B. In like manner, but replacing the 3-cyclohexyl-1-propyn-3-ol with (S)-1-octyn-3-ol, prepared according to Preparation 5.B., there was prepared (S)-3-t-butyldimethylsilyloxyoct-1-yne.

C. Similarly, but starting instead with other suitable compounds of formula XIX, prepared according to Preparation 5.C. or 6.B., the following compounds of formula XX are prepared:
(S)-3-t-butyldimethylsilyloxy-1-decyne;
(S)-3-t-butyldimethylsilyloxy-1-tridecyne;
(3S,5R)-3-t-butyldimethylsilyloxy-5-methyl-1-nonyne;
(S)-3-t-butyldimethylsilyloxy-1-nonyne;
(S)-3-t-butyldimethylsilyloxy-4-phenyl-1-butyne;
(S)-3-t-butyldimethylsilyloxy-5-phenyl-1-pentyne;
(S)-3-t-butyldimethylsilyloxy-4-m-trifluoromethylphenyl-1-butyne;
(S)-3-t-butyldimethylsilyloxy-4-endo-bicyclo[3.1.0]hex-6-yl-1-butyne;
(S)-3-t-butyldimethylsilyloxy-4-exo-bicyclo[3.1.0]hex-6-yl-1-butyne;
(S)-3-t-butyldimethylslyloxy-3-cyclopentyl-1-propyne;
(S)-3-t-butyldimethylsilyloxy-3-cyclooctyl-1-propyne;
(S)-3-t-butyldimethylsilyloxy-4-cyclopentyl-1-butyne; and
(S)-3-t-butyldimethylsilyloxy-4-cyclohexyl-1-butyne.

D. Similarly, but starting instead with racemic compounds of formula XVII, prepared according to Preparation 3, the following racemic compounds of formula XX are prepared:
3-t-butyldimethylsilyloxy-1-octyne;
3-t-butyldimethylsilyloxy-1-decyne;
3-t-butyldimethylsilyloxy-1-tridecyne;
3-t-butyldimethylsilyloxy-1-nonyne;
3-t-butyldimethylsilyloxy-4-phenyl-1-butyne;
3-t-butyldimethylsilyloxy-5-phenyl-1-pentyne;
3-t-butyldimethylsilyloxy-4-m-trifluoromethylphenyl-1-butyne;
3-t-butyldimethylsilyloxy-4-endo-bicyclo[3.1.0]hex-6-yl-1-butyne;
3-t-butyldimethylsilyloxy-4-exo-bicyclo[3.1.0]hex-6-yl-1-butyne;
3-t-butyldimethylsilyloxy-3-cyclopentyl-1-propyne;
3-t-butyldimethylsilyloxy-3-cyclohexyl-1-propyne;
3-t-butyldimethylsilyloxy-3-cyclooctyl-1-propyne;
3-t-butyldimethylsilyloxy-4-cyclopentyl-1-butyne;
3-t-butyldimethylsilyloxy-4-cyclohexyl-1-butyne;
3-t-butyldimethylsilyloxy-3-methyl-3-cyclobutyl-1-propyne; and
3-t-butyldimethylsilyloxy-3-methyl-3-cyclopentyl-1-propyne.

PREPARATION 8

Preparation of
(3'S,1R,2S,3R,6S)-Spiro[2-(3'-t-butyldimethylsilyloxy-3'-cyclohexylprop-1'-ynyl)-3-hydroxybicyclo[4.2.0]octane-7,2'-[1.3]dioxolane] (VIII),
(3'S,1S,2R,3S,6R)-Spiro[2-(3't-butyldimethylsilyloxy-3'-cyclohexylprop-1'-ynyl)-3-hydroxybicyclo[4.2.0]octane-7,2'-[1.3]dioxolane] (IV) and Related Compounds of Formula VIII and IX A. To a mixture of 21 g (S)-3-t-butyldimethylsilyloxy-3-cyclohexyl-1-propyne prepared according to Preparation 7 in 100 ml tetrahydrofuran at 0° C. under argon atmosphere was added over 20 min 60 ml 1.26M n-butyllithium in hexane. The resulting solution was cooled to −78° C. and a solution of 5.5 g of spiro[3-oxatricyclo[5.2.0.0$^{2,4}$]nonane-8,2'-[1.3]dioxolan] in 25 ml tetrahydrofuran was added. To this stirred mixture at −78° C. was added 2.5 ml boron trifluoride etherate dropwise over a 25 min period. To this mixture was added 25 ml saturated sodium sulfate solution. The resulting mixture was warmed to room temperature and it was extracted thoroughly with ethyl acetate. This solution was dried over sodium sulfate and was concentrated in vacuo to give an oily residue. Volatiles were removed on a Kugelrohr distillation device at 95° C. (0.1 mm Hg) to leave 9.28 g of a residue, which was further purified by flash chromatography on silica gel using 1.8% acetone-dichloromethane. This procedure gave 5.87 g of a mixture of the title compounds as an oil.

B. In like manner, but replacing the 3-t-butyldimethylsilyloxy-3-cyclohexyl-1-propyne with other appropriate compounds of formulas XIX and XXII, prepared as described in Preparation 5 and 6, the following mixtures of compounds VIII and IX were prepared:
(3'S,1R,2S,3R,6S)-spiro[2-(3'-t-butyldimethylsilyloxyoct-1-ynyl)-3-hydroxybicyclo[4.2.0]octane-7,2'-[1.3]dioxolan] and
(3'S,1S,2R,3S,6R)-spiro[2-(3'-t-butyldimethylsilyloxyoct-1-ynyl)-3-hydroxybicyclo[4.2.0]octane-7,2'-[1.3]dioxolan].

C. Similarly, but starting with other appropriate compounds of formulas XXI and VI or VII, the following mixtures of compounds VIII and IX are prepared:
(3'S,1R,2S,3R,6S)-spiro[2-(3'-t-butyldimethylsilyloxydec-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-dec-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-tridec-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-tridec-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-tridec-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-5'-methylnon-1'-ynyl)-3-hydroxybicylo[4.2.0]octane-7,2'-[1.3]dioxolan];

(3'S,1R,2S,3R,6S)-spiro[2-(3'-t-butyldimethylsilyloxy-non-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-non-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-phenylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-phenylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-5'-phenylpent-1'-ynyl)-3-hydroxybicyclo[4.2.0]octane-7,2'-[1.3]dixolan], and (3'S,1S,2R,3S,6R)-spiro[2-(3'-t-butyldimethylsilyloxy-5'-phenylpent-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-methyl-4'-phenylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-methyl-4'-phenylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-m-trifluoromethylphenylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-m-trifluoromethylphenylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-endo-bicyclo[3.1.0]hex-6-ylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-endo-bicyclo[3.1.0]hex-6-ylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-xo-bicyclo[3.1.0]hex-6-ylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-xo-bicyclo[3.1.0]hex-6-ylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-methyl-3'-cyclobutylprop-1 α -ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-methyl-3'-cyclobutylprop-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-methyl-3'-cyclopentylprop-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-methyl-3'-cyclopentylprop-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-cyclopentylprop-1'-ynyl)-3hydroxybicyclo[4.2.0]octane-7,2'-[1.3]dioxolan], and (3'S,1S,2R,3S,6R)-spiro[2-(3'-t-butyldimethylsilyloxy-3'-cyclopentylprop-1'-ynyl)-3-hydroxybicyclo[4.2.0]octane-7,2'-[1.3]dioxolan]; (3'S,1R,2S,3R,6S)-spiro[2-(3'-t-butyldimethylsilyloxy-3'-cyclooctylprop-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-cyclooctylprop-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-cyclopentylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-cyclopentylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-cyclohexylbut-1'-ynyl)-3-hydroxybicyclo[4.2.0]octane-7,2'-[1.3]dioxolan]; and (3'S,1S,2R,3S,6R)-spiro[2-(3'-t-butyldimethylsilyloxy-4'-cyclohexylbut-1'-ynyl)-3-hydroxybicyclo[4.2.0]octane-7,2'-[1.3]dioxolan].

PREPARATION 9

Preparation of (3'S,1R,2S,3R,6S)-Spiro[2-(3'-t-butyldimethylsilyloxy-3'-cyclohexylprop-1'-ynyl)-3-hydroxybicyclo[4.2.0]octan-7,2'-[1.3]dioxolane] and (3'S,1S,2R,3S,6R)-Spiro[2-(3't-butyldimthylsilyloxy-3'-cyclohexylprop-1'-ynyl)-3-hydroxybicyclo[4.2.0]octan-7,2'-[1.3]dioxolane] and Related Compounds of Formulas XII and XIII A. To a mixture of 500 mg of the diastereomeric mixture of the above title compounds obtained as described in Preparation 8, in 15 ml diethyl ether was added 472 mg dicobalt octacarbonyl. The resulting solution was stirred at 23° C. for 1 hr. The mixture was diluted with 20 ml diethyl ether and the resulting solution was filtered through 10 g silica gel. The filtrate was concentrated to an oil which was purified by flash chromatography using 13% ethyl acetate-hexane to give two components: A (high $R_f$) and B (low $R_f$). Component A (350 mg) was dissolved in 20 ml acetone-water (9:1), to which was added 1.34 g ceric ammonium nitrate. After 2 min. this mixture was diluted with 50 ml water. The product was isolated by extraction with diethyl ether. After drying and evaporation there was obtained 182 mg of (3'S,1R,2S,3R,6S)-Spiro[2-(3'-t-butyldimethylsilyloxy-3'-cyclohexylprop-1'-ynyl)-3-hydroxybicyclo[4.2.0]octane-7,2'-[1.3]dioxolane] as an oil: CIMS m/z 452 (M+NH$_4$+). Calcd. for $C_{25}H_{42}SiO_4$: C, 69.08, H, 9.74. Found: C, 69.22; H, 9.97. Similarly component B (325 mg) was converted to (3'S,1S,2R,3S,6R)-Spiro[2-(3'-t-butyldimethylsilyloxy-3'-cyclohexylprop-1'-ynyl)-3-hydroxybicyclo[4.2.0]octane-7,2'-[1.3]dioxolane] as an oil: CIMS m/z 452 (M+NH$_4$+). Calcd. for $C_{25}H_{42}SiO_4$: C, 69.08, H, 9.74. Found: C, 69.22; H, 9.97.

B. In like manner, but starting instead with other diastereomeric mixtures of compounds VIII and IX, the following individual enantiomers XII and XIII were obtained:

(3'S,1S,2R,3S,6R)-spiro[2-(3'-t-butyldimethylsilyloxy-oct-1'-ynyl)-3-hydroxybicyclo-[4.2.0]octane-7,2'-[1.3]dioxolan], and (3'S,1R,2S,3R,6S)-spiro[2-(3'-t-butyldimethylsilyloxy-oct-1'-ynyl)-3-hydroxybicyclo[4.2.0]octane-7,2'-[1.3]dioxolan].

C. Similarly, other compounds of formulas XII and XIII are prepared using the mixtures of VIII and IX from Preparation 8.C.:

(3'S,1R,2S,3R,6S)-spiro[2-(3'-t-butyldimethylsilyloxy-dec-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-dec-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-tridec-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-tridec-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-5'-methylnon-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-5'-methylnon-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-non-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-non-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-phenylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-phenylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-5'-phenylpent-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-5'-phenylpent-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-methyl-4'-phenylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-methyl-4'-phenylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-m-trifluoromethylphenylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-m-trifluoromethylphenylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-endo-bicyclo[3.1.0]hex-6-ylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-endo-bicyclo[3.1.0]hex-6-ylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-xo-bicyclo[3.1.0]hex-6-ylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-xo-bicyclo[3.1.0]hex-6-ylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-methyl-3'-cyclobutylprop-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-methyl-3'-cyclobutylprop-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-methyl-3'-cyclopentylprop-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-methyl-3'-cyclopentylprop-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'-cyclopentylprop-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'-cyclopentylprop-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-3'cyclooctylprop-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-3'cyclooctylprop-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-cyclopentylbut-1'-ynyl)-3-hydroxybicyclo[4.2.0]octane-7,2'-[1.3]dioxolan], and (3'S,1S,2R,3S,6R)-spiro[2-(3'-t-butyldimethylsilyloxy-4'-cyclopentylbut-1'-ynyl)-3-hydroxybicyclo[4.2.0]octane-7,2'-[1.3]dioxolan];

(3'S,1R,2S,3R,6S)-spiro[2-(3'-t-butyldimethylsilyloxy-4'-cyclohexylbut-1'-ynyl)-3-hydroxybicyclo[4.2.0]octane-7,2'-[1.3]dioxolan]; and (3'S,1S,2R,3S,6R)-spiro[2-(3'-t-butyldimethylsilyloxy-4'-cyclohexylbut-1'-ynyl)-3-hydroxybicyclo[4.2.0]octane-7,2'-[1.3]dioxolan].

PREPARATION 10

Preparation of (3'S,1R,2S,3R,6S)-Spiro[2-(3'-tertbutyldimethylsilyloxy-3'-cyclohexylprop-1-ynyl)-3-hydroxybicyclo[4.2.0]octane-7,2'-[1.3]dioxolan], (3'R,1S,2R,3S,6R)-Spiro-[2-(3'-tert-butyldimethylsilyloxy-3'-cyclohexylprop-1'-ynyl)-3-hydroxybicyclo[4.2.0]octane-7,2'-[1.3]dioxolan] and Related Individual Enantiomers of Formulas XII and XIII A. A mixture of 2.25 g (3'S*,1R*,2S*,3R*,6S*)spiro[2-(3'-tert-butyldimethylsilyloxy-3'-cyclohexylprop-1'-ynyl)-3-hydroxybicyclo[4.2.0]octane-7,2'-[1.3]dioxolan], 20 ml ethyldiisopropylamine, 0.76 g 4-dimethylaminopyridine, and 3.65 g (R)-(—)-1-naphthylethylisocyanate is stirred at 45° C. for 8 hours. The ethyldiisopropylamine is removed by vacuum evaporation and the residue is dissolved in 100 ml of ethyl acetate. This solution is washed with two 25 ml-portions of 1N hydrochloric acid, and 25 ml water. After drying over sodium sulfate the solvent is removed by evaporation to leave a residue, which was further purified by silica gel flash chromatography using ethyl acetate-dichloromethane-hexane (7.5:22.5:70). This gave in order of elution:

1.31 g of (3'S,1R,2S,3R,6S)-spiro[2-(3'-tert-butyldimethylsilyloxy-3'-cyclohexylprop-1'-ynyl)-3-O-[(R)-1-naphthylethylcarbamoyl]bicyclo[4.2.0]octane-7,2'-

[1.3]dioxolan], mp 57°–59° C., $[\alpha]_D^{25}$ −25.4° (C=1, CHCl$_3$), 1.32 g of (3'R,1R,2S,3R,6R)-spiro[2-(3'-tert-butyldimethylsilyloxy-3'-cyclohexylprop-1'-ynyl)-3-O-[(R)-1-napthylethylcarbamoyl]bicyclo[4.2.0]octane-7,2'-[1.3]dioxolan], mp 107°–109° C., $[\alpha]_D^{25}$ −24.5° C.

Similarly prepared by starting with (3'S*,1S*,2R*,3S*,6R*)spiro[2-(3'-tert-butyldimethylsilyloxy-3'cyclohexylprop-1'-ynyl)-3-[(R)-1-naphthylethylcarbamoyl]bicyclo[4.2.0]octane-7,2'-[1.3]dioxolan] were:

(3'R,1S,2R,3S,6R)-spiro[2-(3'-tert-butyldimethylsilyloxy-3'-cyclohexylprop-1'-ynyl)-3-[(R)-1-naphthylethylcarbamoyl]bicyclo[4.2.0]octane-7,2'-[1.3]dioxolan], mp 81°–83° C., $[\alpha]_D^{25}$ +25°(C+1,CHCl$_3$);

(3'S,1S,2R,3S,6R)-spiro[2-(3'-tert-butyldimethylsilyloxy-3'-cyclohexylprop-1'-ynyl)-3-O-[(R)-1-naphthylethylcarbamoyl]bicyclo[4.2.0]octane-7.2'-[1.3]dioxolan], mp 139°–141° C., $[\alpha]_D^{25}$ −28.4°.

To stirred mixture of 0.3 g lithium aluminum hydride in 50 ml tetrahydrofuran at 0° C. was added a solution of 1.25 g of (3'S,1R,2S,3R,6S)-spiro[2-(3'-tert-butyldimethylsilyloxy-3'-cyclohexylprop-1'-ynyl)-3-O-[(R)-1-naphthylethylcarbanoyl]bicyclo[4.2.0]octane-7,2'-[1.3]dioxolan] in 10 ml tetrahydrofuran. This mixture was heated at reflux for 1 hour. After cooling to 23° C. the mixture was worked up by sequential dropwise addition of 0.5 ml water, 0.5 ml 15% sodium hydroxide solution, and 1.5 ml water. The resulting solid was separated by filtration and the filtrate was evaporated in vacuo. The residue was dissolved in 100 ml ethyl acetate and this solution was washed with two 20 ml portions water and then was dried over sodium sulfate. Evaporation gave a residue that was purified by silica gel flash chromatography using ethyl acetate-hexane (15:85) to give (3'S,1R,2S,3R,6S)-spiro[2-(3'-tert-butyldimethylsilyloxy-3'-cyclohexylprop-1'-ynyl)-3-hydroxybicyclo[4.2.0]octane-7,2'-[1,3]dioxolan], $[\alpha]_D^{25}$ +7.95° (C=0.3, CHCl$_3$).

B. Similarly prepared were:

(3'R,1S,2R,3S,6R)-spiro[2-(3'-tert-butyldimethylsilyloxy-3'-cyclohexylprop-1'-ynyl)-3-hydroxybicyclo[4.2.0]octane-7,2'-[1,3]dioxolan], $[\alpha]_D^{25}$ 0° (C=0.3, CHCl$_3$).

(3'R,1R,2S,3R,6S)-spiro[2-(3'-tert-butyldimethylsilyloxy-3'-cyclohexylprop-1'-ynyl)-3-hydroxybicyclo[4.2.0]octane-7,2'-[1,3]dioxolan], $[\alpha]_D^{25}$ +56.6° (C=0.4, CHCl$_3$).

(3'S,1S,2R,3S,6R)-spiro[2-(3'-tert-butyldimethylsilyloxy-3'-cyclohexylprop-1'-ynyl)-3-hydroxybicyclo[4.2.0]octane-7,2'-[1,3]dioxolan], $[\alpha]_D^{25}$ −54.0° (C=0.5, CHCl$_3$).

C. In like manner, the following individual compounds of formulas XII and XIII are obtained:

(3'S,1R,2S,3R,6S)-spiro[2-(3'-tert-butyldimethylsilyloxyoct-1'-ynyl)-3-hydroxybicyclo[4.2.0]octane-7,2'-[1.3]dioxolan];

(3'R,1S,2R,3S,6R)-spiro[2(3'-tert-butyldimethylsilyloxyoct-1'-ynyl)-3-hydroxybicyclo[4.2.0]octane-7,2'-[1.3]dioxolan];

(3'R,1R,2S,3R,6S)-spiro[2-(3'-tert-butyldimethylsilyloxyoct-1'-ynyl)-3-hydroxybicyclo[4.2.0]octane-7,2'-[1.3]dioxolan];

(3'S,1S,2R,3S,6R)-spiro[2-(3'-tert-butyldimethylsilyloxyoct-1'-ynyl)-3-hydroxybicyclo[4.2.0]octane-7,2'-[1.3]dioxolan];

(3'S,1R,2S,3R,6S)-spiro[2-(3'-tert-butyldimethylsilyloxydec-1'-ynyl)-3-hydroxybicyclo[4.2.0]octane-7,2'-[1.3]dioxolan];

(3'R,1S,2R,3S,6R)-spiro[2-(3'-tert-butyldimethylsilyloxydec-1'-ynyl)-3-hydroxybicyclo[4.2.0]octane-7,2'-[1.3]dioxolan];

(3'R,1R,2S,3R,6S)-spiro[2-(3'-tert-butyldimethylsilyloxydec-1'-ynyl)-3-hydroxybicyclo[4.2.0]octane-7,2'-[1.3]dioxolan];

(3'S,1S,2R,3S,6R)-spiro[2-(3'-tert-butyldimethylsilyloxydec-1'-ynyl)-3-hydroxybicyclo[4.2.0]octane-7,2'-[1.3]dioxolan];

(3'S,1R,2S,3R,6S)-spiro[2-(3'-tert-butyldimethylsilyloxytridec-1'-ynyl)-3-hydroxybicyclo[4.2.0]octane-7,2'-[1.3]dioxolan];

(3'R,1S,2R,3S,6R)-spiro[2-(3'-tert-butyldimethylsilyloxytridec-1'-ynyl)-3-hydroxybicyclo[4.2.0]octane-7,2'-[1.3]dioxolan];

(3'S,1R,2S,3R,6S)-spiro[2-(3'-tert-butyldimethylsilyloxytridec-1'-ynyl)-3-hydroxybicyclo[4.2.0]octane-7,2'-[1.3]dioxolan];

(3'S,1S,2R,3S,6R)-spiro[2-(3'-tert-butyldimethylsilyloxytridec-1'-ynyl)-3-hydroxybicyclo[4.2.0]octane-7,2'-[1.3]dioxolan];

(3'S,1R,2S,3R,6S)-spiro[2-(3'-tert-butyldimethylsilyloxy-5'-methylnon-1'-ynyl)-3-hydroxybicyclo[4.2.0]octane-7,2'-[1.3]dioxolan];

(3'R,1S,2R,3S,6R)-spiro[2-(3'-tert-butyldimethylsilyloxy-5'-methylnon-1'-ynyl)-3-hydroxybicyclo[4.2.0]octane-7,2'-[1.3]dioxolan];

(3'R,1R,2S,3R,6S)-spiro[2-(3'-tert-butyldimethylsilyloxy-5'-methylnon-1'-ynyl)-3-hydroxybicyclo[4.2.0]octane-7,2'-[1.3]dioxolan];

(3'S,1S,2R,3S,6R)-spiro[2-(3'-tert-butyldimethylsilyloxy-5'-methylnon-1'-ynyl)-3-hydroxybicyclo[4.2.0]octane-7,2'-[1.3]dioxolan];

(3'S,1S,2R,3S,6R)-spiro[2-(3'-tert-butyldimethylsilyloxy-non-1'-ynyl)-3-hydroxybicyclo[4.2.0]octane-7,2'-[1.3]dioxolan];

(3'R,1S,2R,3S,6R)-spiro[2-(3'-tert-butyldimethylsilyloxy-non-1'-ynyl)-3-hydroxybicyclo[4.2.0]octane-7,2'-[1.3]dioxolan];

(3'R,1R,2S,3R,6S)-spiro[2-(3'-tert-butyldimethylsilyloxy-non-1'-ynyl)-3-hydroxybicyclo[4.2.0]octane-7,2'-[1.3]dioxolan];

(3'S,1S,2R,3S,6R)-spiro[2-(3'-tert-butyldimethylsilyloxy-non-1'-ynyl)-3-hydroxybicyclo[4.2.0]octane-7,2'-[1.3]dioxolan];

(3'S,1R,2S,3R,6S)-spiro[2-(3'-tert-butyldimethylsilyloxy-4'-phenylbut-1'-ynyl)-b 3-hydroxybicyclo[4.2.0]octane-7,2'-[1.3]dioxolan];

(3'R,1S,2R,3S,6R)-spiro[2-(3'-tert-butyldimethylsilyloxy-4'-phenylbut-1'-ynyl)-3-hydroxybicyclo[4.2.0]octane-7,2'-[1.3]dioxolan];

(3'R,1R,2S,3R,6S)-spiro[2-(3'-tert-butyldimethylsilyloxy-4'-phenylbut-1'-ynyl)-3-hydroxybicyclo[4.2.0]octane-7,2'-[1.3]dioxolan];

(3'S,1S,2R,3S,6R)-spiro[2-(3'-tert-butyldimethylsilyloxy-4'-phenylbut-1'-ynyl)-3-hydroxybicyclo[4.2.0]octane-7,2'-[1.3]dioxolan];

(3'S,1R,2S,3R,6S)-spiro[2-(3'-tert-butyldimethylsilyloxy-5'-phenylpent-1'-ynyl)-3-hydroxybicyclo[4.2.0]octane-7,2'-[1.3]dioxolan];

(3'R,1S,2R,3S,6R)-spiro[2-(3'-tert-butyldimethylsilyloxy-5'-phenylpent-1'-ynyl)-3-hydroxybicyclo[4.2.0]octane-7,2'-[1.3]dioxolan];

(3'R,1R,2S,3R,6S)-spiro[2-(3'-tert-butyldimethyl-silyloxy-5'-phenylpent-1'-ynyl)-3-hydroxybicyclo[4.2.0]octane-7,2'-[1.3]dioxolan];
(3'S,1S,2R,3S,6R)-spiro[2-(3'-tert-butyldimethyl-silyloxy-5'-phenylpent-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-3'-methyl-4'-phenylbut-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-3'-methyl-4'-phenylbut-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-3'-methyl-4'-phenylbut-1'-ynyl)-3-hydroxybicyclo[4.2.0]octane-7,2'-[1.3]dioxolan];
(3'S,1S,2R,3S,6R)-spiro[2-(3'-tert-butyldimethyl-silyloxy-3'-methyl-4'-phenylbut-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-4'-m-trifluoromethylphenylbut-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-4'-m-trifluoromethylphenylbut-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-4'-m-trifluoromethylphenylbut-1'-ynyl)-3-hydroxybicyclo[4.2.0]octane-7,2'-[1.3]dioxolan];
(3'S,1S,2R,3R,6R)-spiro[2-(3'-tert-butyldimethyl-silyloxy-4'-m-trifluoromethylphenylbut-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-4'-endo-bicyclo[3.1.0]hex-61-ylbut-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-4'-endo-bicyclo[3.1.0]hex-6-ylbut-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-4'-endo-bicyclo[3.1.0]hex-6-ylbut-1'-ynyl)-3-hydroxybicyclo[4.2.0]octane-7,2'-[1.3]dioxolan];
(3'S,1S,2R,3S,6R)-spiro[2-(3'-tert-butyldimethyl-silyloxy-4'-endo-bicyclo[3.1.0]hex-6-ylbut-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-4'-exo-bicyclohex-6-ylbut-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-4'-exo-bicyclohex-6-ylbut-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-4'-exo-bicyclohex-6-ylbut-1'-ynyl)-3-hydroxybicyclo[4.2.0]octane-7,2'-[1.3]dioxolan];
(3'S,1S,2R,3S,6R)-spiro[2-(3'-tert-butyldimethyl-silyloxy-4'-exo-bicyclohex-6-ylbut-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-3'-methyl-3'-cyclobutylprop-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-3'-methyl-3'-cyclobutylprop-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-3'-methyl-3'-cyclobutylprop-1'-ynyl)-3-hydroxybicyclo[4.2.0]octane-7,2'-[1.3]dioxolan];
(3'S,1S,2R,3S,6R)-spiro[2-(3'-butyldimethylsilyloxy-3'-methyl-3'-cyclobutylprop-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-3'-methyl-3'-cyclopentylprop-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-3'-methyl-3'-cyclopentylprop-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-3'-methyl-3'-cyclopentylprop-1'-ynyl)-3-hydroxybicyclo[4.2.0]octane-7,2'-[1.3]dioxolan];
(3'S,1S,2R,3S,6R)-spiro[2-(3'-tert-butyldimethyl-silyloxy-3'-methyl-3'-cyclopentylprop-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-3'-cyclopentylprop-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-3'-cyclopentylprop-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-3'-cyclopentylprop-1'-ynyl)-3-hydroxybicyclo[4.2.0]octane-7,2'-[1.3]dioxolan];
(3'S,1S,2R,3S,6R)-spiro[2-(3'-tert-butyldimethyl-silyloxy-3'-cyclopentylprop-1'-ynyl)-3-hydroxybicyclo[4.2.0]octane-7,2'-[1.3]dioxolan];
(3'S,1R,2S,3R,6S)-spiro[2-(3'-tert-butyldimethyl-silyloxy-3'-cyclooctylprop-1'-ynyl)-3-hydroxybicyclo[4.2.0]octane-7,2'-[1.3]dioxolan];
(3'R,1S,2R,3S,6R)-spiro[2-(3'-tert-butyldimethyl-silyloxy-3'-cyclooctylprop-1'-ynyl)-3-hydroxybicyclo[4.2.0]octane-7,2'-[1.3]dioxolan];
(3'R,1R,2S,3R,6S)-spiro[2-(3'-tert-butyldimethyl-silyloxy-3'-cyclooctylprop-1'-ynyl)-3-hydroxybicyclo[4.2.0 octane-7,2'-[1.3]dioxolan]; and
(3'S,1S,2R,3S,6R)-spiro[2-(3'-tert-butyldimethyl-silyloxy-3'-cyclooctylprop-1'-ynyl)-3-hydroxybicyclo[4.2.0]octane-7,2'-[1.3]dioxolan];

PREPARATION 11

Preparation of (3'S,1R,2S,3R,6S)-2-(3'hydroxy-3'-cyclohexylprop-1'-ynyl)-3-hydroxybicyclo[4.2.0]octan-7-one and Related Compounds of Formulas XIV and XV A. A solution of 182 mg of the (3'S,1R,2S, 3R,6S)cyclohexylpropynyl acetal product of Preparation 9.A. or of Preparation 10.A., 1 ml of acetonitrile, 0.2 ml of water and 0.2 ml of 2N sulfuric acid was stirred at ambient temperature for 16 hours. The reaction was quenched by neutralization with aqueous sodium bicarbonate and the mixture was extracted with diethyl ether. The extracts were dried with magnesium sulfate, evaporated to dryness and the residue was purified by short column silica-gel chromatography. Elution with ethyl acetate-hexane (7:3), gave 94 mg (3'S,1R,2S,3R,6S)-2-(3'-hydroxy-3'-cyclohexylprop-1'-ynyl)-3-hydroxybicyclo[4.2.0]octan-7-one, m.p. 93°–98° C.

B. In like manner, but starting with other appropriate compounds of Formula XII, the following compound of formula XIV were obtained:
(3'S,1R,2S,3R,6S)-2-(3'-hydroxyoct-1'-ynyl)-3-hydroxybicyclo[4.2.0]octan-7-one;
(3'S,1R,2S,3R,6S)-2-(3'-hydroxydec-1'-ynyl)-3-hydroxybicyclo[4.2.0]octan-7-one;
(3'S,1R,2S,3R,6S)-2-(3'-hydroxytridec-1'-ynyl)-3-hydroxybicyclo[4.2.0]octan-7-one;
(3'S,5'R,2S,3R,6S)-2-(3'-hydroxy-5'-methyl-non-1'-ynyl)-3-hydroxybicyclo[4.2.0]octan-7-one;

(3'S(,1R*,2S*,3R*,6S*)-2-(3'-hydroxyoct-1'-ynyl)-3-hydroxybicyclo[4.2.0]octan-7-one;

(3'S*,1R*,2S*,3R*,6S*)-2-(3'-hydroxydec-1'-ynyl)-3-hydroxybicyclo[4.2.0]octan-7-one;

(3'S*,1R*,2S*,3R*,6S*)-2-(3'-hydroxytridec-1'-ynyl)-3-hydroxybicyclo[4.2.0]octan-7-one;

(3'S*,5'R*,1R*,2S*,3R*,6S*)-2-(3'-hydroxy-5'-methylnon-1'-ynyl)-3-hydroxybicyclo[4.2.0]octan-7-one;

(3'S*,1R*,2S*,3R*,6S*)-2-(3'-hydroxynon-1'-ynyl)-3-hydroxybicyclo[4.2.0]octan-7one;

(3'S,1R,2S,3R,6S)-2-(3'-hydroxy-4'-phenylbut-1'-ynyl)-3-hydroxybicyclo[4.2.0]octan-7-one;

(3'S,1R,2S,3R,6S)-2-(3'-hydroxy-5'-phenylbut-1'-ynyl)-3-hydroxybicyclo[4.2.0]octan-7-one;

(3'S,1R,2S,3R,6S)-2-(3'-hydroxy-3'-methyl-4'-phenylbut-1'-ynyl)-3-hydroxybicyclo[4.2.0]octan-7-one;

(3'S,1R,2S,3R,6S)-2-(3'-hydroxy-4'-m-trifluoromethylphenylbut-1'-ynyl)-3-hydroxybicyclo[4.2.0]octan-7-one;

(3'S*,1R*,2S*,3R*,6S*)-2-(3'-hydroxy-4'-phenylbut-1'-ynyl)-3-hydroxybicyclo[4.2.0]octan-7-one;

(3'S*,1R*,2S*,3R*,6S*)-2-(3'-hydroxy-5'-phenylpent-1'-ynyl)-3-hydroxybicyclo[4.2.0]octan-7-one;

(3'S*,1R*,2S*,3R*,6S*)-2-(3'-hydroxy-3'-methyl-4-phenylbut-1'-ynyl)-3-hydroxybicyclo[4.2.0]octan-7-one;

(3'S*,1R*,2S*,3R*,6S*)-2-(3'-hydroxy-4'-m-trifluoromethylphenylbut-1'-ynyl)-3-hydroxybicyclo[4.2.0]-octan-7-one;

(3'S,1R,2S,3R,6S)-2-(3'-hydroxy-4'-endo-bicyclo[3.1.0]hex-6-ylbut-1'ynyl)-3-hydroxybicyclo[4.2.0]octan-7-one;

(3'S,1R,2S,3R,6S)-2-(3'-hydroxy-4'-exo-bicyclo[3.1.0]hex-6-ylbut-1'ynyl)-3-hydroxybicyclo[4.2.0]octan-7-one;

(3'S,1R,2S,3R,6S)-2-(3'-hydroxy-3'-methyl-3'-cyclobutylprop-1'-ynyl)-3-hydroxybicyclo[4.2.0]octan-7-one;

(3'S,1R,2S,3R,6S)-2-(3'-hydroxy-3'-methyl-3'-cyclopentylprop-1'-ynyl-3-hydroxybicyclo[4.2.0]octan-7-one;

(3'S,1R,2S,3R,6S)-2-(3'-hydroxy-3'-cyclopentylprop-1'-ynyl)-3-hydroxybicyclo[4.2.0]octan-7-one;

(3'S,1R,2S,3R,6S)-2-(3'-hydroxy-3'-cyclooctylprop-1'-ynyl)-3-hydroxybicyclo[4.2.0]octan-7-one;

(3'S,1R,2S,3R,6S)-2-(3'-hydroxy-3'-cyclopentylprop-1'-ynyl)-3-hydroxybicyclo[4.2.0]octan-7-one;

(3'S,1R,2S,3R,6S)-2-(3'-hydroxy-4'-cyclopentylbut-1'-ynyl)-3-hydroxybicyclo[4.2.0]-octan-7-one;

(3'S,1R,2S,3R,6S)-2-(3'-hydroxy-4'-cyclohexylbut-1'-ynyl)-3-hydroxybicyclo[4.2.0]-octan-7-one;

(3'S*,1R*,2S*,3R*,6S*)-2-(3'-hydroxy-4'-endobicyclo[3.1.0]hex-6-ylbut-1'-ynyl)-3-hydroxybicyclo[4.2.0]octan-7-one;

(3'S*,1R*,2S*,3R*,6S*)-2-(3'-hydroxy-4'-exo-bicyclo[3.1.0]hex-6-ylbut-1'-ynyl-3-hydroxybicyclo[4.2.0]octan-7-one;

(3'S*,1R*,2S*,3R*,6S*)-2-(3'-hydroxy-3'-methyl-3'-cyclobutylprop-1'-ynyl)-3-hydroxybicyclo[4.2.0]octan-7-one;

(3'S*,1R*,2S*,3R*,6S*)-2-(3'-hydroxy-3'-methyl-3'-cyclopentylprop-1'-ynyl)-3-hydroxybicyclo[4.2.0]octan-7-one;

(3'S*,1R*,2S*,3R*,6S*)-2-(3'-hydroxy-3'-cyclopentylprop-1'-ynyl)-3-hydroxybicyclo[4.2.0]octan-7-one;

(3'S*,1R*,2S*,3R*,6S*)-2-(3'-hydroxy-4'-cyclopentylbut-1'-ynyl)-3-hydroxybicyclo[4.2.0]-octan-7-one;

and (3'S*,1R*,2S*,3R*,6S*)-2-(3'-hydroxy-4'-cyclohexylbut-1'-ynyl)-3-hydroxybicyclo[4.2.0]-octan-7-one.

C. In a similar manner, but starting with other appropriate compounds of formula XIII, the following compounds of formula XV were obtained:

(3'S,1S,2R,3S,6R)-2-(3'-hydroxyoct-1'-ynyl)-3-hydroxybicyclo[4.2.0]octan-7-one;

(3'S,1S,2R,3S, 6R)-2-(3'-hydroxydec-1'-ynyl)-3-hydroxybicyclo[4.2.0]octan-7-one;

(3'S,1S,2R,3S,6R)-2-(3'-hyroxytridec-1'-ynyl)-3-hydroxybicyclo[4.2.0]octan-7-one;

(3'S,5'R,1S,2R,3S,6R)-4-[2-(3'-hydroxy-5'-methylnon1'-ynyl)-3-hydroxybicyclo[4.2.0]octan-7-one;

(3'S,1S,2R,3S,6R)-2-(3'-hydroxynon-1'-ynyl)-3-hydroxybicyclo[4.2.0]octan-7-one;

(3'S*,1S*,2R*,3S*,6R*)-2-(3'-hydroxyoct-1'-ynyl)-3-hydroxybicyclo[4.2.0]octan-7-one;

(3'S*,1S*,2R*,3S*,6R*)-2-(3'-hydroxydec-1'-ynyl)-3-hydroxybicyclo[4.2.0]octan-7-one;

(3'S*,1S*,2R*,3S*,6R*)-2-(3'-hydroxytridec-1'-ynyl)-3-hydroxybicyclo[4.2.0]octan-7-one;

(3'S*,5'R*,1S*,2R*,3R*6R*)-2-(3'-hydroxy-5'-methylnon-1'-ynyl)-3-hydroxybicyclo[4.2.0]octan-7-one;

(3'S*,1S*,2R*,3S*,6R*)-2-(3'-hydroxynon-1'-ynyl)-3-hydroxybicyclo[4.2.0]octan-7-one;

(3'S,1S,2R,3S,6R)-2-(3'-hydroxy-4'-phenylbut-1'-ynyl)-3-hydroxybicyclo[4.2.0]octan-7-one;

(3'S,1S,2R,3S,6R)-2-(3'-hydroxy-5'-phenyl]pent-1'-ynyl)-3-hydroxybicyclo[4.2.0]octan-7-one;

(3'S,1S,2R,3S,6R)-2-(3'-hydroxy-3'-methyl-4'-phenylbut-1'-ynyl)-3-hydroxybicyclo[4.2.0]octan-7-one;

(3'S,1S,2R,3S,6R)-2-(3'-hydroxy-4'-m-trifluoromethylphenylbut-1'-ynyl)-3-hydroxybicyclo[4.2.0]octan-7-one;

(3'S*,1S*,2R*,3S*,6R*)-2-(3'-hydroxy-4'-phenylbut-1'-ynyl)-3-hydroxybicyclo[4.2.0]octan-7-one;

(3'S*,1S*2R*,3S*,6R*)-2-(3'-hydroxy-5'-phenylpent-1'-ynyl)-3-hydroxybicyclo[4.2.0]octan-7-one;

(3'S*,1S*,2R*,3S*,6R*)-2-(3'-hydroxy-3'-methyl-4'-phenylbut-1'-ynyl)-3-hydroxybicyclo[4.2.0]octan-7-one;

(3'S*,1S*,2R*,3S*,6R*)-2-(3'-hydroxy-4'-m-triflurorometylphenylbut-1'-ynyl)-3-hydroxybicyclo[4.2.0]octan-7-one;

(3'S,1S,2R,3S,6R)-2-(3'-hydroxy-4'-endo-bicyclo[3.1.0]hex-6-ylbut-1'-ynyl)-3-hydroxybicyclo[4.2.0]octan-7-one;

(3'S,1S,2R,3S,6R)-2-(3'-hydroxy-4'-exobicyclo[3.1.0]hex-6-ylbut-1'-ynyl)-3-hydroxybicyclo[4.2.0]octan-7-one;

(3'S,1S,2R,3S,6R)-3'-hydroxy-3'-methyl-3'-cyclobutylprop-1'-ynyl)-3-hydroxybicyclo[4.2.0]-octan-7-one;

(3'S,1S,2R,3S,6R)-2-(3'-hydroxy-3'-methyl-3'-cyclopentylprop-1'-ynyl)-3-hydroxybicyclo[4.2.0]octan-7-one;

(3'S,1S,2R,3S,6R)-2-(3'-hydroxy-3'-cyclopentylprop-1'-ynyl)-3-hydroxybicyclo[4.2.0]-octan-7-one;

(3'S,1S,2R,3S,6R)-2-(3'-hydroxy-4'-cyclopentylbut-1'-ynyl)-3-hydroxybicyclo[4.2.0]octan-7-one;

(3'S,1S,2R,3S,6R)-2-(3'-hydroxy-3'-cyclopentylprop-1'-ynyl)-3-hydroxybicyclo[4.2.0]-octan-7-one;

(Z)-(3'S,1S,2R,3S,6R)-2-(3'-hydroxy-4'-cyclohexylbut-1'-ynyl)-3-hydroxybicyclo[4.2.0]-octan-7-one;

(3'S*,1S*,2R*,3S*,6R*)-2-(3'-hydroxy-4'-endobicyclo[3.1.0]hex-6-ylbut-1'ynyl)-3-hydroxybicyclo[4.2.0]-octan-7-one;

(3'S*,1S*,2R*,3S*,6R*)-2-(3'-hydroxy-4'-exo-bicyclo[3.1.0]hex-6-ylbut-1'-ynyl)-3-hydroxybicyclo[4.2.0]octan-7-one;

(3'S*,1S*,2R*,3S*,6R*)-2-(3'-hydroxy-3'-methyl-3'-cyclobutyprop-1'-ynyl)-3-hydroxybicyclo[4.2.0]octan-7-one;

(3'S*,1S*,2R*,3S*,6R*)-2-(3'-hydroxy-3'-methyl-3'-cyclopentyl]prop-1'-ynyl)-3-hydroxybicyclo[4.2.0]octan-7-one;

(3'S*,1R*,2R*,6R*)-2-(3'-hydroxy-3'-cyclopentylprop-1'-ynyl)-3-hydroxybicyclo[4,2.0]-octan-7-one;

(3'S*,1S*,2R*,3S*,6R*)-2-(3'-hydroxy-4'-cyclopentylbut-1'-ynyl)-3-hydroxybicyclo[4.2.0]-octan-7-one;

(3'S*,1S*,2R*,3S*,6R*)-2-(3'-hydroxy-3'-cyclohexylprop-1'-ynyl)-3-hydroxybicyclo[4.2.0]-octan-7-one; and (3'S*,1S*,2R*,3S*,6R*)-2-(3'-hydroxy-4'-cyclohexylbut-1'-ynyl)-3-hydroxybicyclo[4.2.0]-octan-7-one.

EXAMPLE 1

Preparation of
(Z)-(3'S,1S,2S,3R,6S)-4-[2-(3'-hydroxy-3'-cyclohexlprop-1'-ynyl)-3-hydroxybicyclo[4.2.0]oct-7-ylidene]-butanoic acid and
(E)-(3'S,1S,2S,3R,6S)-4-[2-(3'-hydroxy-3'cyclohexylprop-1'-ynyl)-3-hydroxybicyclo[4.2.0]oct-7-ylidene]-butanoic acid and Related Compounds of Formulas (1), (2) and (3) in which $R_1$ is $CO_2H$.

A. A stock solution of dimsyl sodium was prepared by dissolving 1.56 g sodium hydride in 65 ml dimethyl sulfoxide at 65° C. under nitrogen. To a stirred slurry of 2.06 g of 3-carboxypropyltriphenylphosphonium bromide in 10 ml of dimethyl sulfoxide under nitrogen was added 9.4 ml of the stock solution of dimsyl sodium. After 20 min at 23° C. a solution of 260 mg of (3'S,1R,2S,3R,6S)-2-(3'-hydroxy-3'-cyclohexylprop-1'-ynyl)-3-hydroxybicyclo[4.2.0]octane-7-one in 1 ml of dimethyl sulfoxide was added in one portion. After 4 h at 23° C. the mixture was poured onto 15 ml 5% sodium carbonate solution. This mixture was washed with two 30 ml portions of ethyl acetate and was then acidified with conc. HCl. The aqueous layer was extracted three times with 50 ml portions of diethyl ether. The combined ether extract was concentrated to 20 ml and this was kept at −20° C. for 2 h. The resulting precipitate was filtered and was discarded. Evaporation of the filtrate gave 430 mg of an oil. This material was purified by silica gel flash chromatography using a solvent mixture of acetic acid-ethyl acetate-hexane (0.25:75:25) to give 337 mg of an oil. Further purification by silica gel flash chromatography using a solvent mixture of acetic acid-methanol-dichloromethane (0.2:5.3:94.5) separated the product mixture into the individual compounds of Formulas 2 and 1, respectively.

The first eluted was:
(E)-(3'S,1S,2S,3R,6S)-4-[2-(3'-hydroxy-3'-cyclohexylprop-1'-ynyl)-3-hydroxybicyclo[4.2.0]oct-7-ylidene]-butyric acid, 138 mg: $[\alpha]_D^{25}+113°(C=0.5, CHCl_3)$.

The second eluted was:
(Z)-(3'S,1S,2S,3R,6S)-4-[2-(3'-hydroxy-3'-cyclohexylprop-1'-ynyl)-3-hydroxybicyclo[4.2.0]oct-7-ylidene]-butyric acid, 138 mg: $[\alpha]_D^{25}+105°$ (C=0.4, CHCl_3).

B. In like manner, but replacing the (3'S,1R,2S,3R,6S)-2-(3'-hydroxy-3'-cyclohexylprop-1'-ynyl)-3-hydroxybicyclo[4.2.0]octane-7-one with other appropriate compounds of formula XIV, obtained as described in Preparation 11.B., the following compounds of formulas (1) and (2) were obtained and separated:

(Z)-(3'S,1S,2S,3R,6S)-4-[2-(3'-hydroxyoct-1'-ynyl)-3-hydroxybicyclo[4.2.0]oct-7-ylidene]butric acid; and (E)-(3'S,1S,2S,3R,6S)-4-[2-(3'-hydroxyoct-1'-ynyl)-3-hydroxybicyclo[4.2.0]oct-7-ylidene]butric acid.

C. Similarly, the following exemplary compounds of Formulas (1) and (2) are obtained:

(Z)-(3'S,1S,2S,3R,6S)-4-[2-(3'-hydroxydec-1'-ynyl)-3-hydroxybicyclo[4.2.0]oct-7-ylidene]butyric acid;

(Z)-(3'S,1S,2S,3R,6S)-5-[2-(3'-hydroxytridec-1'-ynyl)-3-hydroxybicyclo[4.2.0]oct-7-ylidene]pentanoic acid;

(Z)-(3'S,5'R,1S,2S,3R,6S)-4-[2-(3'-hydroxy-5'-methyl-non-1'-ynyl)-3-hydroxybicyclo[4.2.0]oct-7-ylidene]butyric acid;

(Z)-(3'S,1S,2S,3R,6S)-4-[2-(3'-hydroxynon-1'-ynyl)-3-hydroxybicyclo[4.2.0]oct-7-ylidene]butyric acid;

(Z)-(3'S,1S,2S,3R,6S)-5-[2-(3'-hydroxyoct-1'-ynyl)-3-hydroxybicyclo[4.2.0]oct-7-ylidene]pentanoic acid;

(Z)-(3'S*,1S*,2S*,3R*,6S*)-4-[2-(3'-hydroxyoct-1'-ynyl)-3-hydroxybicyclo[4.2.0]oct-7-ylidene]butyric acid;

(Z)-(3'S*,1S*,2S*,3R*,6S*)-4-[2-(3'-hydroxydec-1'-ynyl)-3-hydroxybicyclo[4.2.0]oct-7-ylidene]butyric acid;

(Z)-(3'S*,1S*,2S*,3R*,6S*)-5-[2-(3'-hydroxytridec-1'-ynyl)-3-hydroxybicyclo[4.2.0]oct-7-ylidene]pentanoic acid;

(Z)-(3'S*,5'R*,1S*,2S*,3R*,6S*)-4-[2-(3'-hydroxy-5'-methyl-non-1'-ynyl)-3-hydroxybicyclo[4.2.0]oct-7-ylidene]butyric acid;

(Z)-(3'S*,1S*,2S*,3R*,6S*)-4-[2-(3'-hydroxynon-1'-ynyl)-3-hydroxybicyclo[4.2.0]oct-7-ylidene]butyric acid;

(Z)-(3'S*,1S*,2S*,3R*,6S*)-5-[2-(3'-hydroxyoct-1'-ynyl)-3-hydroxybicyclo[4.2.0]oct-7-ylidene]pentanoic acid.

(Z)-(3'S,1S,2S,3R,6S)-4-[2-(3'-hydroxy-4'-phenylbut-1'-ynyl)-3-hydroxybicyclo[4.2.0]oct-7-ylidene]butyric acid;

(Z)-(3'S,1S,2S,3R,6S)-4-[2-(3'-hydroxy-5'-phenylpent-1'-ynyl)-3-hydroxybicyclo[4.2.0]oct-7-ylidene]butyric acid;

(Z)-(3'S,1S,2S,3R,6S)-5-[2-(3'-hydroxy-3'-methyl-4'-phenylut-1'-ynyl)-3-hydroxybicyclo[4.2.0]oct-7-ylidene]pentanoic acid;

(Z)-(3'S,1S,2S,3R,6S)-5-[2-(3'-hydroxy-4'-m-trifluoromethylphenylbut-1'-ynyl)-3-hydroxybicyclo[4.2.0]oct-7-ylidene]-pentanoic acid;

(Z)-(3'S*,1S*,2S*,3R*,6S*)-4-[2-(3'-hydroxy-4'-phenylbut-1'-ynyl)-3-hydroxybicyclo[4.2.0]-oct-7-ylidene]butyric acid;

(Z)-(3'S*,1S*,2S*,3R*,6S*)-4-[2-(3'-hydroxy-5'-phenylpent-1'-ynyl)-3-hydroxybicyclo[4.2.0]-oct-7-ylidene]butyric acid;

(Z)-(3'S*,1S*,2S*,3R*,6S*)-5-[2-(3'-hydroxy-3'-methyl-4-phenylbut-1'-ynyl)-3-hydroxybicyclo[4.2.0]oct-7-ylidene]pentanoic acid;

(Z)-(3'S*,1S*,2S*,3R*,6S*)-5-[2-(3'-hydroxy-4'-m-trifluoromethylphenylbut-1'-ynyl)-3-hydroxybicyclo[4.2.0]oct-7-ylidene]pentanoic acid;

(Z)-(3'S,1S,2S,3R,6S)-4-[2-(3'-hydroxy-4'-endobicyclo[3.1.0]hex-6-ylbut-1'-ynyl)-3-hydroxybicyclo[4.2.0]-oct-7-ylidene]butyric acid;

(Z)-(3'S,1S,2S,3R,6S)-5-[2-(3'-hydroxy-4'-endobicyclo[3.1.0]hex-6-ylbut-1'-ynyl)-3-hydroxybicyclo[4.2.0]oct-7-ylidene]pentanoic acid;

(Z)-(3'S,1S,2S,3R,6S)-4-[2-(3'-hydroxy-4'-exobicyclo[3.1.0]hex-6-ylbut-1'-ynyl)-3-hydroxybicyclo[4.2.0]oct-7-ylidene]butyric acid;

(Z)-(3'S,1S,2S,3R,6S)-4-[2-(3'-hydroxy-3'-methyl-3'-cyclobutylprop-1'-ynyl)-3-hydroxybicyclo[4.2.0]oct-7-ylidene]butyric acid;

(Z)-(3'S,1S,2S,3R,6S)-4-[2-(3'-hydroxy-3'-methyl-3'-cyclopentylprop-1'-ynyl)-3-hydroxybicyclo[4.2.0]oct-7-ylidene]butyric acid;

(Z)-(3'S,1S,2S,3R,6S)-5-[2-(3'-hydroxy-3'-cyclopentylprop-1'-ynyl)-3-hydroxybicyclo[4.2.0]oct-7-ylidene]pentanoic acid;

(Z)-(3'S,1S,2S,3R,6S)-4-[2-(3'-hydroxy-3'-cyclopentylprop-1'-ynyl)-3-hydroxybicyclo[4.2.0]oct-7-ylidene]butyric acid;

(Z)-(3'S,1S,2S,3R,6S)-4-[2-(3'-hydroxy-4'-cyclopentylbut-1'-ynyl)-3-hydroxybicyclo[4.2.0]oct-7-ylidene]butyric acid;

(Z)-(3'S,1S,2S,3R,6S)-5-[2-(3'-hydroxy-3'-cyclohexylprop-1-ynyl)-3-hydroxybicyclo[4.2.0]oct-7-ylidene]pentanoic acid;

(Z)-(3'S,1S,2S,3R,6S)-4-[2-(3'-hydroxy-4'-cyclohexylbut-1'-ynyl)-3-hydroxybicyclo[4.2.0]oct-7-ylidene]butric acid;

(Z)-(3'S,1S,2S,3R,6S)-4-[2-(3'-hydroxy-4'-cyclohexylbut-1'-ynyl)-3-hydroxybicyclo[4.2.0]oct-7-ylidene]butric acid.

(Z)-(3'S,1S,2S,3R,6S)-4-[2-(3'-hydroxy-4'-cyclohexylbut-1'-ynyl)-3-hydroxybicyclo[4.2.0]oct-7-ylidene]pentanoic acid;

(Z)-(3'S*,1S*,2S*,3R*,6S*)-4-[2-(3'-hydroxy-4'-endobicyclo[3.1.0]hex-6-ylbut-1'-ynyl)-3-hydroxybicyclo[4.2.0]oct-7-ylidene]butyric acid;

(Z)-(3'S*,1S*,2S*,3R*,6S*)-5-[2-(3'-hydroxy-4'-endobicyclo[3.1.0]hex-6-ylbut-1'-ynyl)-3-hydroxybicyclo[4.2.0]oct-7-ylidene]pentanoic acid;

(Z)-(3'S*,1S*,2S*,3R*,6S*)-4-[2-(3'-hydroxy-4'-exobicyclo[3.1.0]hex-6-ylbut-1'-ynyl)-3-hydroxybicyclo[4.2.0]-oct-7-ylidene]butyric acid;

(Z)-(3'S*,1S*,2S*,3R*,6S*)-4-[2-(3'-hydroxy-3'-methyl-3'-cyclobutylprop-1'-ynyl)-3-hydroxybicyclo[4.2.0]oct-7-ylidene]butyric acid;

(Z)-(3'S*,1S*,2S*,3R*,6S*)-4-[2-(3'-hydroxy-3'-methyl-3'-cyclopentylprop-1'-ynyl)-3-hydroxybicyclo[4.2.0]oct-7-ylidene]butyric acid;

(Z)-(3'S*,1S*,2S*,3R*,6S*)-5-[2-(3'-hydroxy-3'-cyclopentylprop-1'-ynyl)-3-hydroxybicyclo[4.2.0]oct-7-ylidene]pentanoic acid;

(Z)-(3'S*,1S*,2S*,3R*,6S*)-4-[2-(3'-hydroxy-3'-cyclopentylprop-1'-ynyl)-3-hydroxybicyclo[4.2.0]oct-7-ylidene]butyric acid;

(Z)-(3'S*,1S*,2S*,3R*,6S*)-4-[2-(3-hydroxy-4'-cyclopentylbut-1'-ynyl)-3-hydroxybicyclo[4.2.0]oct-7-ylidene]butyric acid;

(Z)-(3'S*,1S*,2S*,3R*,6S*)-5-[2-(3'-hydroxy-3'-cyclohexylprop-1'-ynyl)-3-hydroxybicyclo[4.2.0]oct-7-ylidene]pentanoic acid;

(Z)-(3'S*,1S*,2S*,3R*,6S*)-4-[2-(3'-hydroxy-4'-cyclohexylbut-1'-ynyl)-3-hydroxybicyclo[4.2.0]oct-7-ylidene]butyric acid;

(Z)-(3'S*,1S*,2S*,3R*,6S*)-5-[2-(3'-hydroxy-4'-cyclohexylbut-1'-ynyl)-3-hydroxybicyclo[4.2.0]octylidene]pentanoic acid;

(E)-(3'S,1S,2S,3R,6S)-4-[2-(3'-hydroxydec-1'-ynyl)-3-hydroxybicyclo[4.2.0]oct-7-ylidene]butyric acid;

(E)-(3'S,1S,2S,3R,6S)-5-[2-(3'-hydroxytridec-1'-ynyl)-3-hydroxybicyclo[4.2.0]oct-7-ylidene]pentanoic acid;

(E)-(3'S,5'R,1S,2S,3R,6S)-4-[2-(3'-hydroxy-5'-methyl-non-1'-ynyl)-3-hydroxybicyclo[4.2.0]oct-7-ylidene]butyric acid;

(E)-(3'S,1S,2S,3R,6S)-4-[2-(3'-hydroxynon-1'-ynyl)-3-hydroxybicyclo[4.2.0]oct-7-ylidene]butyric acid;

(E)-(3'S,1S,2S,3R,6S)-5-[2-(3'-hydroxyoct-1'-ynyl)-3-hydroxybicyclo[4.2.0]oct-7-ylidene]pentanoic acid;

(E)-(3'S*,1S*,2S*,3R*,6S*)-4-[2-(3'-hydroxyoct-1'-ynyl)-3-hydroxybicyclo[4.2.0]oct-7-ylidene]butyric acid;

(E)-(3'S*,1S*,2S*,3R*,6S*)-4-[2-(3'-hydroxydec-1'-ynyl)-3-hydroxybicyclo[4.2.0]oct-7-ylidene]butyric acid;

(E)-(3'S*,1S*,2S*,3R*,6S*)-5-[2-(3'-hydroxytridec-1'-ynyl)-3-hydroxybicyclo[4.2.0]oct-7-ylidene]pentanoic acid;

(E)-(3'S*,5'R*,1S*,2S*,3R*,6S*)-4-[2-(3'-hydroxy-5'-methyl-non-1'-ynyl)-3-hydroxybicyclo[4.2.0]oct-7-ylidene]butyric acid;

(E)-(3'S*,1S*,2S*,3R*,6S*)-4-[2-(3'-hydroxynon-1'-ynyl)-3-hydroxybicyclo[4.2.0]oct-7-ylidene]butyric acid;

(E)-(3'S*,1S*,2S*,3R*,6S*)-5-[2-(3'-hydroxynon-1'-ynyl)-3-hydroxybicyclo[4.2.0]oct-7-ylidene]pentanoic acid;

(E)-(3'S,1S,2S,3R,6S)-4-[2-(3'-hydroxy-4'-phenylbut-1'-ynyl)-3-hydroxybicyclo[4.2.0]oct-7-ylidene]butyric acid;

(E)-(3'S,1S,2S,3R,6S)-4-[2-(3'-hydroxy-5'-phenylpent-1'-ynyl)-3-hydroxybicyclo[4.2.0]oct-7-ylidene]butyric acid;

(E)-(3'S,1S,2S,3R,6S)-5-[2-(3'-hydroxy-3'-methyl-4'-phenylbut-1'-ynyl)-3-hydroxybicyclo[4.2.0]oct-7-ylidene]pentanoic acid;

(E)-(3'S,1S,2S,3R,6S)-5-[2-(3'-hydroxy-4'-m-trifluoromethylphenylbut-1'-ynyl)-3-hydroxybicyclo[4.2.0]oct-7-ylidene]pentanoic acid;

(E)-(3'S*,1S*,2S*,3R*,6S*)-4-[2-(3'-hydroxy-4'-phenylbut-1'-ynyl)-3-hydroxybicyclo[4.2.0]oct-7-ylidene]butyric acid;

(E)-(3'S*,1S*,2S*,3R*,6S*)-4-[2-(3'-hydroxy-5'-phenylpent-1'-ynyl)-3-hydroxybicyclo[4.2.0]oct-7-ylidene]butyric acid;

(E)-(3'S*,1S*,2S*,3R*,6S*)-5-[2-(3'-hydroxy-3'-methyl-4'-phenylbut-1'-ynyl)-3-hydroxybicyclo[4.2.0]oct-7-ylidene]-pentanoic acid;

(E)-(3'S*,1S*,2S*,3R*,6S*)-5-[2-(3'-hydroxy-4'-m-trifluoro-methylphenylbut-1-ynyl)-3-hydroxybicyclo[4.2.0]oct-7-ylidene]pentanoic acid;

(E)-(3'S,1S,2S,3R,6S)-4-[2-(3'-hydroxy-4'-endobicyclo[3.1.0]hex-6-ylbut-1-ynyl)-3-hydroxybicyclo[4.2.0]oct-7-ylidene]butyric acid;

(E)-(3'S,1S,2S,3R,6S)-5-[2-(3'-hydroxy-4'-endobicyclo[3.1.0]hex-6-ylbut-1'-ynyl)-3-hydroxybicyclo[4.2.0]oct-7-ylidene]pentanoic acid;

(E)-(3'S,1S,2S,3R,6S)-4-[2-(3'-hydroxy-4'-exobicyclo[3.1.0]hex-6-ylbut-1'-ynyl)-3-hydroxybicyclo[4.2.0]oct-7-ylidene]butyric acid;

(E)-(3'S,1S,2S,3R,6S)-4-[2-(3'-hydroxy-3'-methyl-3'-cyclobutylprop-1'-ynyl)-3-hydroxybicyclo[4.2.0]oct-7-ylidene]butyric acid;

(E)-(3'S,1S,2S,3R,6S)-4-[2-(3'-hydroxy-3'-methyl-3'-cyclopentylprop-1-ynyl)-3-hydroxybicyclo[4.2.0]oct-7-ylidene]butyric acid;

(E)-(3'S,1S,2S,3R,6S)-5-[2-(3'-hydroxy-3'-cyclopentylprop-1'-ynyl)-3-hydroxybicyclo[4.2.0]oct-7-ylidene]pentanoic acid;

(E)-(3'S,1S,2S,3R,6S)-4-[2-(3'-hydroxy-3'-cyclooctyl-prop-1'-ynyl)-3-hydroxybicyclo[4.2.0]oct-7-ylidene]-butyric acid;
(E)-(3'S,1S,2S,3R,6S)-4-[2-(3'-hydroxy-3'-cyclopentyl-prop-1'-ynyl)-3-hydroxybicyclo[4.2.0]oct-7-ylidene]-butyric acid;
(E)-(3'S,1S,2S,3R,6S)-4-[2-(3'-hydroxy-4'-cyclopentyl-but-1'-ynyl)-3-hydroxybicyclo[4.2.0]oct-7-ylidene]-butyric acid;
(E)-(3'S,1S,2S,3R,6S)-5-[2-(3'-hydroxy-3'-cyclohexyl-prop-1'-ynyl)-3-hydroxybicyclo[4.2.0]oct-7-ylidene]-pentanoic acid;
(E)-(3'S,1S,2S,3R,6S)-4-[2-(3'-hydroxy-4'-cyclohexyl-but-1'-ynyl)-3-hydroxybicyclo[4.2.0]oct-7-ylidene]-butyric acid;
(E)-(3'S,1S,2S,3R,6S)-5-[2-(3'-hydroxy-4'-cyclohexyl-but-1-ynyl)-3-hydroxybicyclo[4.2.0]oct-7-ylidene]-pentanoic acid.
(E)-(3'S*,1S*,2S*,3R*,6S*)-4-[2-(3'-hydroxy-4'-endobicyclo[3.1.0]hex-6-ylbut-1'-ynyl)-3-hydroxybicyclo[4.2.0]oct-7-ylidene]butyric acid;
(E)-(3'S*,1S*,2S*,3R*,6S*)-5-[2-(3'-hydroxy-4'-endobicyclo[3.1.0]hex-6-ylbut-1'-ynyl)-3-hydroxybicyclo[4.2.0]oct-7-ylidene]pentanoic acid;
(E)-(3'S*,1S*,2S*,3R*,6S*)-4-[2-(3'-hydroxy-4'-exobicyclo[3.1.0]hex-6-ylbut-1'-ynyl)-3-hydroxybicyclo[4.2.0]-oct-7-ylidene]butyric acid;
(E)-(3'S*,1S*,2S*,3R*,6S*)-4-[2-(3'-hydroxy-3'-methyl-3'-cyclobutylprop-1'-ynyl)-3-hydroxybicyclo[4.2.0]oct-7-ylidene]butyric acid;
(E)-(3'S*,1S*,2S*,3R*,6S*)-4-[2-(3'-hydroxy-3'-methyl-3'-cyclopentylprop-1'-ynyl)-3-hydroxybicyclo[4.2.0]oct-7-ylidene]butyric acid;
(E)-(3'S*,1S*,2S*,3R*,6S*)-5-[2-(3'-hydroxy-3'-cyclopentylprop-1'-ynyl)-3-hydroxybicyclo[4.2.0]oct-7-ylidene]pentanoic acid;
(E)-(3'S*,1S*,2S*,3R*,6S*)-4-[2-(3'-hydroxy-3'-cyclopentylprop-1'-ynyl)-3-hydroxybicyclo[4.2.0]oct-7-ylidene]butyric acid;
(E)-(3'S*,1S*,2S*,3R*,6S*)-4-[2-(3'-hydroxy-3'-cyclopentylprop-1'-ynyl)-3-hydroxybicyclo[4.2.0]oct-7-ylidene]butyric acid;
(E)-(3'S*,1S*,2S*,3R*,6S*)-4-[2-(3'-hydroxy-4'-cyclopentylbut-1'-ynyl)-3-hydroxybicyclo[4.2.0]oct-7-ylidene]butyric acid;
(E)-(3'S*,1S*,2S*,3R*,6S*)-5-[2-(3'-hydroxy-3'-cyclohexylprop-1'-ynyl)-3-hydroxybicyclo[4.2.0]oct-7-ylidene]pentanoic acid;
(E)-(3'S*,1S*,2S*,3R*,6S*)-4-[2-(3'-hydroxy-4'-cyclohexylbut-1'-ynyl)-3-hydroxybicyclo[4.2.0]oct-7-ylidene]butyric acid; and
(E)-(3'S*,1S*,2S*,3R*,6S*)-5-[2-(3'-hydroxy-4'-cyclohexylbut-1'-ynyl)-3-hydroxybicyclo[4.2.0]oct-7-ylidene]pentanoic acid.

D. In like manner using the appropriate compounds of formula XV, obtained as described in Preparation 10.C, the following compounds of Formula (3) were obtained:
(Z)-(3'S,1R,2R,3S,6R)-4-[2-(3'-hydroxy-3'-cyclohexyl-prop-1'-ynyl)-3-hydroxybicyclo[4.2.0]oct-7-ylidene]-butyric acid;
(Z)-(3'S,1R,2R,3S,6R)-5-[2-(3'-hydroxy-3'-cyclohexyl-prop-1'-ynyl)-3-hydroxybicyclo[4.2.0]oct-7-ylidene]-pentanoic acid; and
(Z)-(3'S,1R,2R,3S,6R)-4-[2-(3'-hydroxyoct-1'-ynyl)-3-hydroxybicyclo[4.2.0]oct-7-ylidene]butyric acid.acid.

E. Similarly, the following compounds of Formula (3) are obtained:

(Z)-(3'S,1S,2S,3R,6S)-4-[2-(3'-hydroxydec-1'-ynyl)-3-hydroxybicyclo[4.2.0]oct-7-ylidene]butyric acid;
(Z)-(3'S,1S,2S,3R,6S)-5-[2-(3'-hydroxytridec-1'-ynyl)-3-hydroxybicyclo[4.2.0]oct-7-ylidene]pentanoic acid;
(Z)-(3'S,5'R,1R,2R,3S,6R)-4-[2-(3'-hydroxy-5'-methyl-non-1'-ynyl)-3-hydroxybicyclo[4.2.0]oct-7-ylidene]-butyric acid;
(Z)-(3'S,1S,2S,3R,6S)-4-[2-(3'-hydroxynon-1'-ynyl)-3-hydroxybicyclo[4.2.0]oct-7-ylidene]butyric acid;
(Z)-(3'S,1S,2S,3R,6S)-5-[2-(3'-hydroxyoct-1'-ynyl)-3-hydroxybicyclo[4.2.0]oct-7-ylidene]pentanoic acid;
(Z)-(3'S*,1R*,2R*,3S*,6R*)-4-[2-(3'-hydroxyoct-1'-ynyl)-3-hydroxybicyclo[4.2.0]oct-7-ylidene]butyric acid;
(Z)-(3'S*,1R*,2R*,3S*,6R*)-4-[2-(3'-hydroxydec-1'-ynyl)-3-hydroxybicyclo[4.2.0]oct-7-ylidene]butyric acid;
(Z)-(3'S*,1R*,2R*,3S*,6R*)-5-[2-(3'-hydroxytridec-1'-ynyl)-3-hydroxybicyclo[4.2.0]oct-7-ylidene]pentanoic acid;
(Z)-(3'S*,5'R*,1R*,2R*,3S*,6R*)-4-[2-(3'-hydroxy-5'-methyl-non-1'-ynyl)-3-hydroxybicyclo[4.2.0]oct-7-ylidene]butyric acid;
(Z)-(3'S*,1R*,2R*,3S*,6R*)-4-[2-(3'-hydroxynon-1'-ynyl)-3-hydroxybicyclo[4.2.0]oct-7-ylidene]butyric acid;
(Z)-(3'S*,1R*,2R*,3S*,6R*)-5-[2-(3'-hydroxyoct-1'-ynyl)-3-hydroxybicyclo[4.2.0]oct-7-ylidene]pentanoic acid.
(Z)-(3'S,1R,2R,3S,6R)-4-[2-(3'-hydroxy-4'-phenylbut-1'-ynyl)-3-hydroxybicyclo[4.2.0]oct-7-ylidene]-butyric acid;
(Z)-(3'S,1R,2R,3W,6R)-4-[2-(3'-hydroxy-5'-phenyl-pent-1'-ynyl)-3-hydroxybicyclo[4.2.0]oct-7-ylidene]-butyric acid;
(Z)-(3'S,1R,2R,3S,6R)-5-[2-(3'-hydroxy-3'-methyl-4'-phenylbut-1'-ynyl)-3-hydroxybicyclo[4.2.0]oct-7-ylidene]pentanoic acid;
(Z)-(3'S,1R,2R,3S,6R)-5-[2-(3'-hydroxy-4'-m-tri-fluoromethylphenylbut-1'-ynyl)-3-hydroxybicyclo[4.2.0]oct-7-ylidene]pentanoic acid;
(Z)-(3'S*,1R*,2R*,3S*,6R*)-4-[2-(3'-hydroxy-4'-phenylbut-1'-ynyl)-3-hydroxybicyclo[4.2.0]oct-7-yldene]butyric acid;
(Z)-(3'S*,1R*,3S*,6R*)-4-[2-(3'-hydroxy-5'-phenyl-pent-1'-ynyl)-3-hydroxybicyclo[4.2.0]oct-7-ylidene]-butyric acid;
(Z)-(3'S*,1R*,2R*,3S*,6R*)-5-[2-(3'-hydroxy-4'-m-tri-fluoro-methylphenylbut-1'-ynyl)-3-hydroxybicyclo[4.2.0]oct-7-ylidene]pentanoic acid;
(Z)-(3'S,1R,2R,3S,6R)-4-[2-(3'-hydroxy-4'-endobicyclo[3.1.0]-hex-6-ylbut-1'-ynyl)-3-hydroxybicyclo[4.2.0]oct-7-ylidene]butyric acid;
(Z)-(3'S,1R,2R,3R,6R)-5-[2-(3'-hydroxy-4'-endobicyclo[3.1.0]hex-6-ylbut-1'-ynyl)-3-hydroxybicyclo[4.2.0]oct-7-ylidene]pentanoic acid;
(Z)-(3'S,1R,2R,3S,6R)-4-[2-(3'-hydroxy-4'-exobicyclo[3.1.0]hex-6-ylbut-1'-ynyl)-3-hydroxybicyclo[4.2.0]oct-7-ylidene]butyric acid;
(Z)-(3'S,1R,2R,3S,6R)-4-[2-(3'-hydroxy-3'-methyl-3'-cyclobutylprop-1'-ynyl)-3-hydroxybicyclo[4.2.0]oct-7-ylidene]butyric acid;
(Z)-(3'S,1R,2R,3S,6R)-4-[2-(3'-hydroxy-3'-methyl-3'-cyclopentylprop-1'-ynyl)-3-hydroxybicyclo[4.2.0]oct-7-ylidene]butyric acid;
(Z)-(3'S,1R,2R,3S,6R)-4-[2-(3'-hydroxy-3'-cyclopentyl-prop-1'-ynyl)-3-hydroxybicyclo[4.2.0]oct-7-ylidene]-butyric acid;

(Z)-(3'S,1R,2R,3S,6R)-4-[2-(3'-hydroxy-3'-cyclopentyl-prop-1'-ynyl)-3-hydroxybicyclo[4.2.0]oct-7-ylidene]-butyric acid;

(Z)-(3'S,1R,2R,3S,6R)-4-[2-(3'-hydroxy-4'-cyclopentyl-prop-1'-ynyl)-3-hydroxybicyclo[4.2.0]oct-7-ylidene]-butyric acid;

(Z)-(3'S,1R,2R,3S,6R)-4-[2-(3'-hydroxy-4'-cyclopentyl-but-1'-ynyl)-3-hydroxybicyclo[4.2.0]oct-7-ylidene]-butyric acid;

(Z)-(3'S,1R,2R,3S,6R)-4-[2-(3'-hydroxy-4'-cyclohexyl-but-1'-ynyl)-3-hydroxybicyclo[4.2.0]oct-7-ylidene]-butyric acid;

(Z)-(3'S,1R,2R,3S,6R)-5-[2-(3'-hydroxy-4'-cyclohexyl-but-1'-ynyl)-3-hydroxybicyclo[4.2.0]oct-7-ylidene]-pentanoic acid;

(Z)-(3'S*,1R*,2R*,3S*,6R*)-4-[2-(3'-hydroxy-4'-endobicyclo[3.1.9]hex-6-ylbut-1'-ynyl)-3-hydroxybicyclo[4.2.0]oct-7-ylidene]butyric acid;

(Z)-(3'S,1R*,2R*,3S*,6R*)-5-[2-(3'-hydroxy-4'-endobicyclo[3.1.0]hex-6-ylbut-1'-ynyl)-3-hydroxybicyclo[4.2.0]oct-7-ylidene]pentanoic acid;

(Z)-(3'S*,1R*,3S*,6R*)-4-[2-(3'-hydroxy-4'-exobicyclo[3.1.0]hex-6-ylbut-1'-ynyl)-3-hydroxybicyclo[4.2.0]oct-7-ylidene]butyric acid;

(Z)-(3'S*,1R*,2R*,3S*,6R*)-4-[2-(3'-hydroxy-3'-methyl-3'-cyclobutylprop-1'-ynyl)-3-hydroxybicyclo[4.2.0]oct-7-ylidene]butyric acid;

(Z)-(3'S*,1R*,2R*,3S*,6R*)-4-[2-(3'-hydroxy-3'-methyl-3'-cyclopentylprop-1'-ynyl)-3-hydroxybicyclo[4.2.0]oct-7-ylidene]butyric acid;

(Z)-(3'S*,1R*,2R*,3S*,6R*)-5-[2-(3'-hydroxy-3'-cyclopentylprop-1'-ynyl)-3-hydroxybicyclo[4.2.0]oct-7-ylidene]pentanoic acid;

(Z)-(3'S*,1R*,2R*,3S*,6R*)-4-[2-(3'-hydroxy-3'-cyclopentylprop-1'-ynyl)-3-hydroxybicyclo[4.2.0]oct-7-ylidene]butyric acid;

(Z)-(3'S*,1R*,2R*,3S*,6R*)-4-[2-(3'-hydroxy-3'-cyclopentylprop-1-ynyl)-3-hydroxybicyclo[4.2.0]-oct-7-ylidene]butyric acid;

(Z)-(3'S*,1R*,2R*,3S*,6R*)-4-[2-(3'-hydroxy-4'-cyclopentylbut-1-ynyl)-3-hydroxybicyclo[4.2.0]oct-7-ylidene]butyric acid;

(Z)-(3'S*,1R*,2R*,3S*,6R*)-4-[2-(3'-hydroxy-3'-cyclohexylprop-1-ynyl)-3-hydroxybicyclo[4.2.0]oct-7-ylidene]butyric acid;

(Z)-(3'S*,1R*,2R*,3S*,6R*)-4-[2-(3'-hydroxy-3'-cyclopentylprop-1'-ynyl)-3-hydroxybicyclo[4.2.0]oct-7-ylidene]butyric acid;

(Z)-(3'S*,1R*,2R*,3S*,6R*)-4-[2-(3'-hydroxy-4'-cyclopentylbut-1'-ynyl)-3-hydroxybicyclo[4.2.0]oct-7-ylidene]butyric acid;

(Z)-(3'S*,1R*,2R*,3S*,6R*)-4-[2-(3'-hydroxy-3'-cyclohexylprop-1'-ynyl)-3-hydroxybicyclo[4.2.0]oct-7-ylidene]butyric acid;

(Z)-(3'S*,1R*,2R*,3S*,6R*)-5-[2-(3'-hydroxy-3'-cyclohexylprop-1'-ynyl)-3-hydroxybicyclo[4.2.0]oct-7-ylidene]pentanoic acid;

(Z)-(3'S*,1R*,2R*,3S*,6R*)-4-[2-(3'-hydroxy-4'-cyclohexylbut-1'-ynyl)-3-hydroxybicyclo[4.2.0]oct-7-ylidene]butyric acid; and (Z)-(3'S*,1R*,2R*,3S*,6R*)-5-[2-(3'-hydroxy-4'-cyclohexylbut-1'-ynyl)-3-hydroxybicyclo[4.2.0]oct-7-lidene]pentanoic acid.

EXAMPLE 2

Preparation of methyl Z-(3'S,1S,2S,3R,6S)-4-[2-(3'-hydroxy-3'-cyclohexy(-prop-1'-ynyl)-3-hydroxybicyclo[4.2.0]oct-7-ylidene]butyrate, related compounds of Formula XXVIII, and other pharmaceutically acceptable esters.

A. To a solution of 0.5 g Z-(3'S,1S,2S,3R,6S)-4-[2-(3'-hydroxy-3'-cyclohexylprop-1'-ynyl)-3-hydroxybicyclo[4.2.0]oct-7-ylidene]butyric acid in 10 ml diethyl ether was added excess etherial diazomethane until the yellow color persisted. Evaporation of solvent gave 0.52 g of the title compound.

B. In like manner, but starting with other appropriate compounds of formulas (1), (2), and (3), the following exemplary esters are obtained:

methyl (Z)-(3'S,1S,2S,3R,6S)-4-[2-(3'-hydroxy-3'-cyclohexylprop-1'-ynyl)-3-hydroxybicyclo[4.2.0]oct-7-ylidene]butyrate;

methyl (Z)-(3S*,1S*,2S*,3R*,6S*)-4-[2-(3'-hydroxy-3'-cycloprop-1'-ynyl)-3-hydroxybicyclo[4.2.0]-oct-7-ylidene]butyrate;

methyl (E)-(3'S,1S,3R,6S)-4-[2-(3'-hydroxy-3'-cyclohexylprop-1'-ynyl)-3-hydroxybicyclo[4.2.0]oct-7-ylidene]butyrate;

methyl (E)-(3'S*,1S*,3R*,6S*)-4-[2-(3'-hydroxy-3'-cyclohexylprop-1'-ynyl)-3-hydroxybicyclo[4.2.0]oct-7-ylidene]butyrate;

methyl (Z)-(3'S,1S,3R,6S)-4-[2-(3'-hydroxy-3'-cyclopentylprop-1'-ynyl)-3-hydroxybicyclo[4.2.0]oct-7-ylidene]butyrate acid; and methyl (Z)-(3'S*,1S*,3R*,6S*)-4-[2-(3'-hydroxy-3'-cyclopentylprop-1'-ynyl)-3-hydroxybicyclo[4.2.0]oct-7-ylildene]butyrate.

EXAMPLE 3

Compounds Wherein $R_1$ is $CH_2OH$

A. Preparation of methyl Z-(3'S,1S,2S,3R,6S)-4-[2-(3'-tert-butyldimethylsilyloxy-3'-cyclohexylprop-1'-ynyl)-3-tert-butyldimethylsilyloxybicycto[4.2.0]oct-7-ylidene]butyrate and related compounds of Formula XXIX.

A mixture of 0.52 g methyl Z-(3'S,1S,2S,3R,6S)-4-[2-(3'-hydroxy-3'-cyclohexylprop-1'-ynyl)-3-hydroxybicyclo[4.2.0]oct-7-ylidene]butyrate, 0.55 g tert-butyldimethylsilyl chloride, 0.18 g 4-dimethylaminopyridene, 2 ml triethylamine and 10 ml dichloromethane was stirred at 23° C. for 24 hours. After dilution with 20 ml of dichloromethane the mixture was washed with 10 ml water, three 20-ml portions of 1N CHl and 10 ml sat. sodium bicarbonate. After drying over sodium sulfate the solvent was removed to give 0.78 of the title compound.

Similarly, but starting with other appropriate esters of Formula XXVIII, the following compounds of Formula XXIX are prepared:

methyl (Z)-(3'S,1S,2S,3R,6S)-5-[2-(3'-tert-butyldimethylsilyloxy-3'-cyclohexylprop-1'-ynyl)-3-tertbutyl-dimethylsilyloxybicyclo[4.2.0]oct-7-ylidene]pentanoate;

methyl (Z)-(3S*,1S*,2S*,3R*,6S*)-4-[2-(3'-tert-butyldimethylsilyloxy-3'-cycloprop-1'-ynyl)-3-tertbutyl-dimethylsilyloxybicyclo-[4.2.0]-oct-7-ylidene]butyrate;

methyl (E)-(3'S,1S,3R,6S)-4-[2-(3'-tert-butyldimethylsilyloxy-3'-cyclohexylprop-1'-ynyl)-3-tert-butyldimethylsilyloxybicyclo[4.2.0]-oct-7-ylilidene]butyrate;

methyl (E)-(3'S*,1S*,3R*,6S*)-4-[2-(3'-tert-butyldimethylsilyloxy-3'-cyclohexylprop-1'-ynyl)-3-tertbutyldimethylsilyloxybicyclo[4.2.0]-oct-7-ylilidene]butyrate;

methyl (Z)-(3'S,1S,3R,6S)-4-[2-(3'-tert-butyldimethylsilyloxy-3'-cyclopentylprop-1'-ynyl)-3-tertbutyldimethylsilyloxybicyclo[4.2.0]-oct-7-ylilidene]butyrate; and methyl (Z)-(3'S*,1S*,3R*,6S*)-4-[2-(3'-tert-butyldimethylsilyloxy-3'-cyclopentylprop-1'-ynyl)-3-tertbutyldimethylsilyloxybicyclo[4.2.0]-oct-7-ylilidene]butyrate.

B. Preparation of Z-(3'S,1S,2S,3R,6S)-4-[2-(3'-tert-butyldimethylsilyloxy-3'-cyclohexylprop-1'-ynyl)-3-tert-butyldimethylsilyloxybicyclo[4.2.0]oct-7-ylidene]-1-butanol and related compounds of Formula XXX.

To a stirred mixture of 0.1 g lithium aluminum hydride in 15 ml diethyl ether is added in dropwise fashion a solution of 0.78 g of methyl Z-(3'S,1S,2S,3R,6S)-4-[2-(3-tert-butyldimethylsilyloxy)-3-tert-butyldimethylsilyloxybicyclo[4.2.0]oct-7-ylidene]butyrate in 5 ml of diethyl ether. This mixture is heated at reflux for 2 h. After cooling the reaction is worked up by sequential dropwise addition of 0.1 ml water, 0.1 ml 15% sodium hydroxide, and 0.3 ml water. The resulting precipitate is removed by filtration. Evaporation of the filtrate gives 0.7 g of the title compound.

In a similar manner, but starting instead with other appropriate compounds of Formula XXIX, prepared according to the method described in paragraph A above, the following compounds of Formula XXX are prepared:

(Z)-(3'S,1S,2S,3R,6S)-5-[2-(3'-tert-butyldimethylsilyloxy-3'-cyclohexylprop-1'-ynyl)-3-tertbutyldimethylsilyloxybicyclo[4.2.0]oct-7-ylidene]-1-pentanol;

(Z)-(3S*,1S*,2S*,3R*,6S*)-4-[2-(3'-tert-butyldimethylsilyloxy-3'-cycloprop-1'-ynyl)-3-tertbutyldimethylsilyloxybicyclo-[4.2.0]-oct-7-ylidene]-1-butanol;

(E)-(3'S,1S,3R,6S)-4-[2-(3'-tert-butyldimethylsilyloxy-3'-cyclohexylprop-1'-ynyl)-3-tert-butyldimethylsilyloxybicyclo[4.2.0]-oct-7-ylidene]-1-butanol;

(E)-(3'S*,1S*,3R*,6S*)-4-[2-(3'-tert-butyldimethylsilyloxy-3'-cyclohexylprop-1'-ynyl)-3-tertbutyldimethylsilyloxybicyclo[4.2.0]-oct-7-ylidene]-1-butanol;

(Z)-(3'S,1S,3R,6S)-4-[2-(3'-tert-butyldimethylsilyloxy-3'-cyclopentylprop-1'-ynyl)-3-tertbutyldimethylsilyloxybicyclo[4.2.0]-oct-7-ylidene]-1-butanol; and (Z)-(3'S*,1S*,3R*,6S*)-4-[2-(3'-tert-butyldimethylsilyloxy-3'-cyclopentylprop-1'-ynyl)-3-tertbutyldimethylsilyloxybicyclo[4.2.0]-oct-7-ylidene]-1-butanol.

C. Preparation of Z-(3'S,1S,2S,3R,6S)-4-(2-(3'hydroxy-3'-cyclohexylprop-1'-ynyl)-3-hydroxybicyclo[4.2.0]oct-7-ylidene]-1-butanol and related compounds of Formulas (1) (2) and (3) in which R₁ is CH₂OH.

To a solution of 0.15 g Z-(3'S,1S,2S,3R,6S)-4-[2-(3-tert-butyldimethylsilyloxy-3'-cyclohexylprop-1'-ynyl)-3-tert-butyldimethylsilyloxybicyclo[4.2.0]oct-7-ylidene]-1-butanol in 3 ml tetrahydrofuran was added 5 ml of a 1M solution of tetrabutylammonium fluoride in tetrahydrofuran. After 12 hours at 23° C. the solution is diluted with 20 ml water and the product is extracted into diethyl ether. Evaporation of the solvent and purification of the product using silica gel flash chromatography with ethyl acetate-hexane (1:1) gave 0.8 g of the title compound.

In like manner, but starting with other compounds of Formula XXX, preparation of which is described in paragraph B of this Example, the following compounds of formulas (1), (2), and (3) in which $R_1$ is CH₂OH are prepared:

(Z)-(3'S,1S,2S,3R,6S)-5-[2-(3'-hydroxy-3'-cyclohexylprop-1'-ynyl)-3-hydroxybicyclo[4.2.0]oct-7-ylidene]-1-pentanol;

(Z)-(3S*,1S*,3R*,6S*)-4-[2-(3'-hydroxy-3'-cycloprop-1'-ynyl)-3-hydroxybicyclo[4.2.0]-oct-7-ylidene]-1-butanol;

(E)-(3'S,1S,3R,6S)-4-[2-(3'-hydroxy-3'-cyclohexylprop-1-ynyl)-3-hydroxybicyclo[4.2.0]oct-7-ylidene]-1-butanol;

(E)-(3'S,1S*,3R*,6S*)-4-[2-(3'-hydroxy-3'-cyclohexylprop-1-ynyl)-3-hydroxybicyclo[4.2.0]-oct-7-ylildene]-1-butanol;

(Z)-(3'S,1S,3R,6S)-4-[2-(3'-hydroxy-3'-cyclopentylprop-1'-ynyl)-3-hydroxybicyclo[4.2.0]oct-7-ylidene]-1-butanol; and (Z)-(3'S*,1S*,3R*,6S*)-4-[2-(3'-hydroxy-3'-cyclopentylprop-1'-ynyl)-3-hydroxybicyclo[4.2.0]-oct-7-ylildene]-1-butanol.

EXAMPLE 4

Preparation of Z-(3'S,1S,2S,3R,6S)-4-[2-(3'-hydroxy-3'-cyclohexylprop-2'-ynyl)-3-hydroxybicyclo[4.2.0]oct-7-ylidene]-1-butanal and related compounds of Formulas (1), (2) and (3) wherein $R_1$ is CHO.

A. To a stirred mixture of 0.25 g pyridinium chlorochromate in 7 ml dichloromethane was added a solution of 0.2 g Z-(3'S,1S,2S,3R,6S)-4-[2-(3'-tert-butyldimethylsilyloxy-3'-cyclohexylprop-1'-ynyl)-3-tert-butyldimethylsilyloxybicyclo[4.2.0]oct-7-ylidene]-1-butanol, prepared according to Example 3.A., in 3 ml dichloromethane. After 4 hours at 23° C. the solution was decanted from the precipitate and was filtered through 10 g florisil with dichloromethane. The filtrate was concentrated to a residue, which was dissolved in 3 ml tetrahydrofuran. To this solution was added 2 ml of a 1M solution of tetrabutylammonium fluoride in tetrahydrofuran. After 16 hours at 23° C. this solution was diluted with 20 ml water and the product was extracted into diethyl ether. Evaporation of solvent followed by silica gel flash chromatography using ethyl acetate-hexane (30:70) gave 0.1 g of the title compound.

B. In a similar manner, but starting with other appropriate compounds of Formula XXX, preparation of which is described in Example 3, the following compounds of Formulas (1), (2), and (3) in which $R_1$ is CHO are prepared:

(Z)-(3'S,1S,3R,6S)-5-[2-(3'-hydroxy-3'-cyclohexylprop-1'-ynyl)-3-hydroxybicyclo[4.2.0]oct-7-ylidene]-1-pentanal;

(Z)-(3S*,1S*,2S*,3R*,6S*)-4-[2-(3'-hydroxy-3'-cycloprop-1'-ynyl)-3-hydroxybicyclo[4.2.0]-oct-7-ylidene]-1-butanal;

(E)-(3'S,1S,3R,6S)-4-[2-(3'-hydroxy-3'-cyclohexylprop-1ynyl)-3-hydroxybicyclo[4.2.0]oct-7-ylidene]-1-butanal;

(E)-(3'S*,1S*,3R*,6S*)-4-[2-(3'-hydroxy-3'-cyclohexylprop-1-ynyl)-3-hydroxybicyclo[4.2.0]oct-7-ylildene]-1-butanal;

(Z)-(3'S,1S,3R,6S)-4-[2-(3'-hydroxy-3'-cyclopentylprop-1-ynyl)-3-hydroxybicyclo[4.2.0]oct-7-ylildene]-1-butanal; and (Z)-(3'S*,1S*,3R*,6S*)-4-[2-(3'-hydroxy-3'-cyclopentylprop-1'-ynyl)-3-hydroxybicyclo[4.2.0]oct-7-ylildene]-1-butanal.

EXAMPLE 5

Preparation of p-Benzamidophenyl Z-(3'S,1S,2S,3R,6S)-4-[2-(3'-hydroxy-3'-cyclohexylprop-1'-ynyl)-3-hydroxybicyclo[4.2.0]oct-7-ylidene]butyrate, and related compounds of Formulas (1), (2), and (3) in which $R_1$ is $CO_2R$.

A. A solution of Z-(3'S,1S,2S,3R,6S)-4-[2-(3'-hydroxy-3'-cyclohexylprop-1'-ynyl)-3-hydroxybicyclo[4.2.0]-oct-7-ylidene]butyric acid (35 mg, 0.101 mmol) in acetone (2.7 mL) was treated with triethylamine (28.1 µL, 0.202 mmol). The solution was cooled to −5° C. under $N_2$ and isobutyl chlorocarbonate (27.3 µL, 0.202 mmol) was added. After 5 min at −5° C., a solution of p-benzamidophenol (109.2 mg, 0.51 mmol) in dry pyridine (1.1 mL) was added. After 3 h at room temperature, the solvent was removed under vacuum. The residue was extracted with dichloromethane and the solid (excess p-benzamidophenol) was removed by filtration. After evaporation of the solvent, the residue was purified by column chromatography using 30% acetone in hexane to afford 12 mg of the title compound. Mass spectrum: m/z=541 (M+). Anal. Calcd for $C_{34}H_{39}O_5N$: C, 75.39; H, 7.26; N, 2.59. Found: C, 75.35; H, 7.12; N, 2.40.

B. In like manner, but starting with other appropriate compounds of Formulas (1), (2), or (3), in which $R_1$ is $CO_2H$ and substituting for the p-benzamidophenol other appropriate substituted phenols, the corresponding exemplary compounds in which $R_1$ is $CO_2R$ are prepared:

p-acetylphenyl (Z)-(3'S,1S,2S,3R,6S)-5-[2-(3'-hydroxy-3'-cyclohexylprop-1'-ynyl)-3-hydroxybicyclo[4.2.0]-oct-7-ylidene]pentanoate;

p-benzoylphenyl (Z)-(3S*,1S*,2S*,3R*,6S*)-4-[2-(3'-hydroxy-3'-cycloprop-1'-ynyl)-3-hydroxybicyclo[4.2.0]-oct-7-ylidene]butyrate;

p-N',N'-dimethylureidophenyl (E)-(3'S,1S,3R,6S)-4-[2-(3'-hydroxy-3'-cyclohexylprop-1-ynyl)-3-hydroxybicyclo[4.2.0]-oct-7-ylildene]butyrate;

p-benzamidophenyl (E)-(3'S*,1S*,3R*,6S*)-4-[2-(3'-hydroxy-3'-cyclohexylprop-1-ynyl)-3-hydroxybicyclo[4.2.0]-oct-7-ylildene]butyrate;

p-benzoylphenyl (Z)-(3'S,1S,3R,6S)-4-[2-(3'-hydroxy-3'-cyclopentylprop-1-ynyl)-3-hydroxybicyclo[4.2.0]-oct-7-ylildene]butyrate; and p-methylureidophenyl (Z)-(3'S*,1S*,3R*,6S*)-4-[2-(3'-hydroxy-3'-cyclopentylprop-1'-ynyl)-3-hydroxybicyclo[4.2.0]-oct-7-ylildene]butyrate.

What we claim is:

1. A compound of formula (1), (2) or (3)

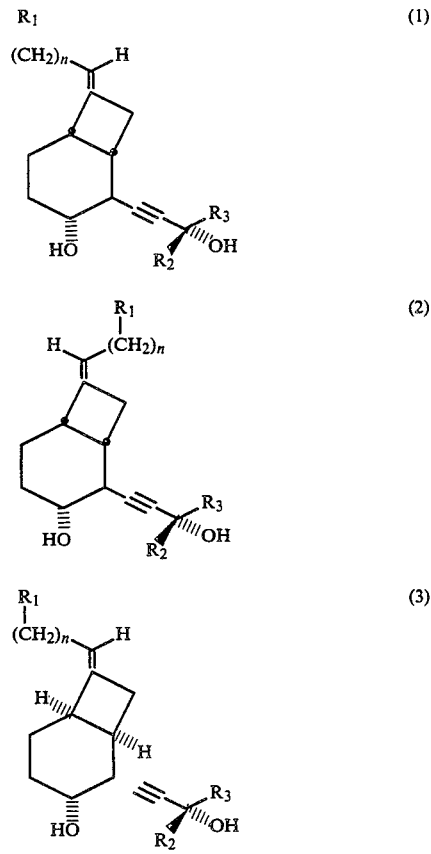

wherein:
n is 2 or 3;
$R_1$ is $CH_2OH$, CHO, $CO_2R$ or $CO_2H$;
$R_2$ is hydrogen or methyl; and
$R_3$ is linear or branched alkyl having 5-10 carbon atoms,

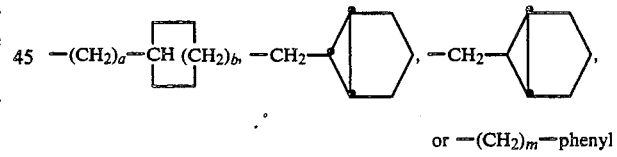

optionally substituted with lower alkyl, lower alkoxy, trifluoromethyl, or halogen,
in which
a is 0, 1 or 2;
b is 3–7;
m is 1 or 2; and
R is

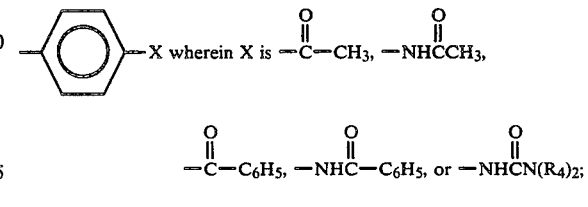

in which each $R_4$ is independently hydrogen or lower alkyl having 1-6 carbon atoms, and the pharmaceutically acceptable, non-toxic salts and esters thereof.

2. A compound of claim 1 wherein n is 2 or 3, $R_1$ is $CO_2H$, $CO_2R$ or CHO; $R_2$ is hydrogen or methyl; and $R_3$ is linear or branched alkyl of 5 to 10 carbons,

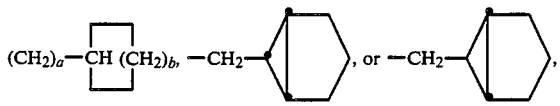

and the pharmaceutically acceptable, non-toxic salts and esters thereof.

3. A compound of claim 2 wherein n is 2 or 3, $R_1$ is CHO, $CO_3R$ or $CO_2H$, $R_2$ is hydrogen or methyl, and $R^3$ is linear or branched alkyl of 5 or 7 carbon atoms,

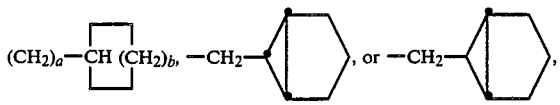

and the pharmaceutically acceptable, non-toxic salts and esters thereof.

4. A compound of claim 3 wherein n is 2 or 3, $R_1$ is $CO_2R$ or $CO_2H$, $R_2$ is hydrogen or methyl, and $R_3$ is n-pentyl, and the pharmaceutically acceptable, non-toxic salts and esters thereof.

5. A compound of claim 3 wherein n is 2 or 3, $R_1$ is $CO_2R$ or $CO_2H$, $R_2$ is hydrogen or methyl, and $R_3$ is

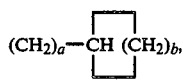

and the pharmaceutically acceptable non-toxic salts and esters thereof.

6. A compound of claim 5 wherein n is 2, $R_1$ is $CO_2H$, $R_2$ is hydrogen, and $R_3$ is

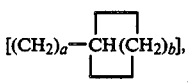

and the pharmaceutically acceptable, non-toxic salts and esters thereof.

7. A compound of claim 6 wherein a is 0 or 1, and the pharmaceutically acceptable non-toxic salts and esters thereof.

8. A compound of claim 7 wherein a is 0 and b is 5, and the pharmaceutically acceptable, non-toxic, salts and esters thereof.

9. A compound of claim 5 wherein n is 3 and a is 0 or 1.

10. A compound of claim 7 in which a is 0 and b is 5, namely (Z)-(3′S,1S,2S,3R,6S)-4-[2-(3′-hydroxy-3′-cyclohexylprop-1′-ynyl)-3-hydroxybicyclo[4.2.0]-oct-7-ylidene]butyric acid, and the pharmaceutically acceptable non-toxic salts and esters thereof.

11. The racemic modification of the compound of claim 10, namely (Z)-(3S*,1S*,2S*,3R*,6S*)-4-[2-(3′-hydroxy-4′-cyclohexyprop-1′-ynyl)-3-hydroxybicyclo[4.2.0]-oct-7-ylidene]butyric acid, and the pharmaceutically acceptable non-toxic salts and esters thereof.

12. The (E)-isomer of the compound of claim 10, namely (E)-(3′S,1S,2S,3R,6S)-4-[2-(3′-hydroxy-3′-cyclohexylprop-1′-ynyl)-3-hydroxybicyclo[4.2.0]-oct-7-ylildene]butyric acid, and the pharmaceutically acceptable non-toxic salts and esters thereof.

13. The (E)-isomer of the compound of claim 11, namely (E)-(3′S*,1S*,2S*,3R*,6S*)-4-[2-(3′-hydroxy-3′-cyclohexylprop-1′-ynyl)-3-hydroxybicyclo[4.2.0]-oct-7-ylildene]butyric acid, and the pharmaceutically acceptable non-toxic salts and esters thereof.

14. A compound of claim 7 in which a is 0 and b is 4, namely (Z)-(3′S,1S,2S,3R,6S)-4-[2-(3′-hydroxy-3′-cyclopentylprop-1′-ynyl)-3-hydroxybicyclo[4.2.0]-oct-7-ylildene]butyric acid, and the pharmaceutically acceptable non-toxic salts and esters thereof.

15. The racemic modification of the compound of claim 14, namely (Z)-(3′S*,1S*,2S*,3R*,6S*)-4-[2-(3′-hydroxy-3′-cyclopentylprop-1′-ynyl)-3-hydroxybicyclo[4.2.0]-oct-7-ylildene]butyric acid, and the pharmaceutically acceptable non-toxic salts and esters thereof.

16. The (E)-isomer of the compound of claim 14, namely (E)-(3′S,1S,2S,3R,6S)-4-[2-(3′-hydroxy-3′-cyclopentylprop-1′-ynyl)-3-hydroxybicyclo[4.2.0]-oct-7-ylildene]butyric acid, and the pharmaceutically acceptable non-toxic salts and esters thereof.

17. The (E)-isomer of the compound of claim 15, namely (E)-(3′S*,1S*,2S*,3R*,6S*)-4-[2-(3′-hydroxy-3′-cyclopentylprop-1′-ynyl)-3-hydroxybicyclo[4.2.0]-oct-7-ylildene]butyric acid, and the pharmaceutically acceptable non-toxic salts and esters thereof.

18. A compound of claim 9 wherein a is 0 and b is 4, namely (Z)-(3′S,1S,3R,6S)-5-[2-(3′-hydroxy-3′-cyclopentylprop-1′-ynyl)-3-hydroxybicyclo[4.2.0]-oct-7-ylildene]pentanoic acid, and the pharmaceutically acceptable non-toxic salts and esters thereof.

19. The racemic modification of the compound of claim 18, namely (Z)-(3′S*,1S*,2S*,3R*,6S*)-5-[2-(3′-hydroxy-3′-cyclopentylprop-1′-ynyl)-3-hydroxybicyclo[4.2.0]-oct-7-ylildene]pentanoic acid, and the pharmaceutically acceptable non-toxic salts and esters thereof.

20. The (E)-isomer of the compound of claim 19, namely (E)-(3′S,1S,2S,3R,6S)-5-[2-(3′-hydroxy-3′-cyclopentylprop-1′-ynyl)-3-hydroxybicyclo[4.2.0 -oct-7-ylildene]pentanoic acid, and the pharmaceutically acceptable non-toxic salts and esters thereof.

21. The (E)-isomer of the compound of claim 19, namely (E)-(3′S*,1S*,2S*,3R*,6S*)-5-[2-(3′-hydroxy-3′-cyclopentylprop-1′-ynyl)-3-hydroxybicyclo[4.2.0]-oct-7-ylildene]pentanoic acid, and the pharmaceutically acceptable non-toxic salts and esters thereof.

22. A compound of claim 9 in which a is 0 and b is 5, namely (Z)-(3′S,1S,2S,3R,6S)-5-[2-(3′-cyclohexylprop-1′-ynyl)-3-hydroxybicyclo[4.2.0]-oct-7-ylildene]pentanoic acid, and the pharmaceutically acceptable non-toxic salts and esters thereof.

23. The racemic modification of the compound of claim 22, namely (Z)-(3′S*,1S*,2S*,3R*,6S*)-5-[2-(3′-cyclopentylprop-1′-ynyl)-3-hydroxybicyclo[4.2.0]-oct-7-ylildene]pentanoic acid, and the pharmaceutically acceptable non-toxic salts and esters thereof.

24. The (E)-isomer of the compound of claim 22, namely (E)-(3′S,1S,2S,3R,6S)-5-[2-(3′-hydroxy-3′-cyclohexylprop-1′-ynyl)-3-hydroxybicyclo[4.2.0]-oct-7-ylildene]pentanoic acid, and the pharmaceutically acceptable non-toxic salts and esters thereof.

25. The (E)-isomer of the compound of claim 23, namely (E)-(3′S*,1S*,2S*, 3R*, 6S*)-5-[2-(3′-hydroxy-3′-cyclohexylprop-1′-ynyl)-3-hydroxybicyclo[4.2.0]-

26. A compound of claim 9 in which a is 0 and b is 4, namely (Z)-(3′S,1R,2R,3S,6R)-5-[2-(3′-hydroxy-3′-cyclopentylprop-1′-ynyl)-3-hydroxybicyclo[4.2.0]-oct-7-ylildene]pentanoic acid, and the pharmaceutically acceptable non-toxic salts and esters thereof.

27. The racemic modification of the compound of claim 26, namely (Z)-(3′S*,1R*,2R*,3S*,6R*)-5-[2-(3′-hydroxy-3′-cyclopentylprop-1′-ynyl)-3-hydroxybicyclo[4.2.0]-oct-7-ylildene]pentanoic acid, and the pharmaceutically acceptable non-toxic salts and esters thereof.

28. A compound of claim 7 in which a is 0 and b is 4, namely (Z)-(3′S,1R,2R,3S,6R)-4-[2-(3′-hydroxy-3′-cyclopentylprop-1′-ynyl)-3-hydroxybicyclo[4.2.0]-oct-7-ylildene]butyric acid, and the pharmaceutically acceptable non-toxic salts and esters thereof.

29. The racemic modification of the compound of claim 28, namely (Z)-(3′S*,1R*,2R*,3S*,6R*)-4-[2-(3′-hydroxy-3′-cyclopentylprop-1′-ynyl)-3-hydroxybicyclo[4.2.0]-oct-7-ylildene]butyric acid, and the pharmaceutically acceptable non-toxic salts and esters thereof.

30. A compound of claim 7 in which a is 0 and b is 5, namely (Z)-(3′S,1R,2R,3S,6R)-4-[2-(3′-hydroxy-3′-cyclohexylprop-1′-ynyl)-3-hydroxybicyclo[4.2.0]-oct-7-ylildene]butyric acid, and the pharmaceutically acceptable non-toxic salts and esters thereof.

31. The racemic modification of the compound of claim 30, namely (Z)-(3′S*,1R*,2R*,3S*,6R*)-4-[2-(3′-hydroxy-3′-cyclohexylprop-1′-ynyl)-3-hydroxybicyclo[4.2.0]-oct-7-ylildene]butyric acid, and the pharmaceutically acceptable non-toxic salts and esters thereof.

32. A compound of claim 9 in which a is 0 and b is 5, namely (Z)-(3′S,1R,2R,3S,6R)-5-[2-(3′-hydroxy-3′-cyclohexylprop-1′-ynyl)-3-hydroxybicyclo[4.3.0]-oct-7-ylildene]pentanoic acid, and the pharmaceutically acceptable non-toxic salts and esters thereof.

33. The racemic modification of the compound of claim 32, namely (Z)-(3′S*,1R*,2R*,3S*,6R*)-5-[2-(3′-hydroxy-3′-cyclohexylprop-1′-ynyl)-3-hydroxybicyclo[4.2.0]-oct-7-ylildene]pentanoic acid, and the pharmaceutically acceptable non-toxic salts and esters thereof.

34. A compound of claim 3 wherein n is 2, $R_1$ is $CO_2H$, $R_2$ is hydrogen, and $R_3$ is —$(CH_2)_m$-phenyl, and the pharmaceutically acceptable non-toxic salts and esters thereof.

35. A compound of claim 34 in which m is 1, namely (Z)-(3′S,1S,2S,3R,6S)-4-[2-(3′-hydroxy-4′-phenylbut-1′-ynyl)-3-hydroxybicyclo[4.2.0]-oct-7-ylildene]butyric acid, and the pharmaceutically acceptable non-toxic salts and esters thereof.

36. The racemic modification of the compound of claim 35, namely (Z)-(3′S*,1S*,2S*,3R*,6S*)-4-[2-(3′-hydroxy-4′-phenylbut-1′-ynyl)-3-hydroxybicyclo[4.2.0]-oct-7-ylildene]butyric acid, and the pharmaceutically acceptable non-toxic salts and esters thereof.

37. The (E)-isomer of the compound of claim 35, namely (E)-(3′S,1S,2S,3R,6S)-4-[2-(3′-hydroxy-4′-phenylbut-1′-ynyl)-3-hydroxybicyclo[4.2.0]-oct-7-ylildene]butyric acid, and the pharmaceutically acceptable non-toxic salts and esters thereof.

38. The racemic modification of the compound of claim 37, namely (E)-(3′S*,1R*,2R*,3S*,6R*)-4-[2-(3′-hydroxy-4′-phenylbut-1′-ynyl)-3-hydroxybicyclo[4.2.0]-oct-7-ylildene]butyric acid, and the pharmaceutically acceptable non-toxic salts and esters thereof.

39. A compound of claim 34 in which m is 1, namely (Z)-(3′S,1R,2R,3S,6R)-4-[2-(3′-hydroxy-4′-phenylbut-1′-ynyl)-3-hydroxybicyclo[4.2.0]-oct-7-ylildene]butyric acid, and the pharmaceutically acceptable non-toxic salts and esters thereof.

40. The racemic modification of the compound of claim 39, namely (Z)-(3′S*,1R*,2R*,3S*,6R*)-4-[2-(3′-hydroxy-4′-phenylbut-1′-ynyl)-3-hydroxybicyclo[4.2.0]-oct-7-ylildene]butyric acid, and the pharmaceutically acceptable non-toxic salts and esters thereof.

41. A compound of claim 3 wherein n is 2, $R_1$ is $CO_2H$, $R_2$ is hydrogen, and $R_3$ is linear or branched alkyl of 5 carbon atoms.

42. A compound of claim 41 which is named (Z)-(3′S,1S,2S,3R,6S)-4-[2-(3′-hydroxyoct-1′-ynyl)-3-hydroxybicyclo[4.2.0]-oct-7-ylildene]butyric acid, and the pharmaceutically acceptable non-toxic salts and esters thereof.

43. The racemic modification of the compound of claim 42, namely (Z)-(3′S*,1S*,2S*,3R*,6S*)-4-[2-(3′-hydroxyoct-1′-ynyl)-3-hydroxybicyclo[4.2.0]-oct-7-ylildene]butyric acid, and the pharmaceutically acceptable non-toxic salts and esters thereof.

44. A compound of claim 41 which is named (Z)-(3′S,1R,2R,3S,6R)-4-[2-(3′-hydroxyoct-1′-ynyl)-3-hydroxybicyclo[4.2.0]-oct-7-ylildene]butyric acid, and the pharmaceutically acceptable non-toxic salts and esters thereof.

45. The racemic modification of the compound of claim 44, namely (Z)-(3′S*,1R*,2R*,3S*,6R*)-4-[2-(3′-hydroxyoct-1′-ynyl)-3-hydroxybicyclo[4.2.0]-oct-7-ylildene]butyric acid, and the pharmaceutically acceptable non-toxic salts and esters thereof.

46. A method for treating cardiovascular disorders in mammals which comprises administering a therapeutically effective amount of a compound of claim 1, or a pharmaceuticlaly acceptable non-toxic salt or ester thereof, to a subject in need of such treatment.

47. The method of claim 46 wherein the disorder is atherosclerosis.

48. The method of claim 46 wherein the disorder involves a thrombotic condition.

49. The method of claim 46 wherein the disorder involves a vasospastic condition.

50. The method of claim 46 wherein the disorder is hypertension.

51. The method of claim 46 wherein the disorder is elevated cholesterol levels.

52. A pharmaceutical composition containing at least one suitable pharmaceutical excipient and a compound of claim 1 or a pharmaceutically acceptable, non-toxic salt or ester thereof.

53. A compound of claim 1 in which n is 2, and the pharmaceutically acceptable non-toxic salts and esters thereof.

54. A compound of claim 1 in which $R_2$ is hydrogen, and the pharmaceutically acceptable, non-toxic salts and esters thereof.

55. A compound of claim 1 in which $R_3$ is

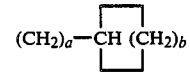

in which a is 0 or 1 and b is 3–7.

* * * * *